(12) United States Patent
Hirakawa et al.

(10) Patent No.: US 8,269,823 B2
(45) Date of Patent: Sep. 18, 2012

(54) IN VIVO IMAGING DEVICE, DISPLAY DEVICE, IMAGING AND DISPLAYING SYSTEM AND INTRA-SUBJECT INDWELLING SYSTEM USING THE SAME

(75) Inventors: Katsumi Hirakawa, Sagamihara (JP); Takeshi Yokoi, Hino (JP); Akio Uchiyama, Yokohama (JP); Shinsuke Tanaka, Hachioji (JP); Hironobu Takizawa, Hachioji (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1147 days.

(21) Appl. No.: 11/632,979

(22) PCT Filed: Jul. 13, 2006

(86) PCT No.: PCT/JP2006/013993
§ 371 (c)(1),
(2), (4) Date: Sep. 24, 2007

(87) PCT Pub. No.: WO2007/007842
PCT Pub. Date: Jan. 18, 2007

(65) Prior Publication Data
US 2008/0117291 A1    May 22, 2008

(30) Foreign Application Priority Data

Jul. 14, 2005    (JP) .................................. 2005-205958

(51) Int. Cl.
*H04N 7/18*    (2006.01)
(52) U.S. Cl. ......................................................... 348/65
(58) Field of Classification Search .................... 348/65; 600/175
See application file for complete search history.

(56) References Cited

U.S. PATENT DOCUMENTS
6,130,717 A * 10/2000 Arai et al. ..................... 348/360
(Continued)

FOREIGN PATENT DOCUMENTS
JP        2001-286433        10/2001
(Continued)

OTHER PUBLICATIONS

Japanese Office Action dated Mar. 16, 2010 together with partial English translation.

(Continued)

*Primary Examiner* — Yves Dalencourt
*Assistant Examiner* — Hee Soo Kim
(74) *Attorney, Agent, or Firm* — Scully, Scott, Murphy & Presser, P.C.

(57) ABSTRACT

An object of the present invention is to continuously display a series of images of the inside of the subject until the intra-body indwelling capsule is placed at the desired site in the subject, and to easily place the intra-body indwelling capsule endoscope at the desired site. The intra-subject indwelling system 1 according to the present invention includes an endoscope device 14 for imaging a first image of the inside of the subject; an intra-body indwelling capsule 2, for imaging a second image of the inside of the subject; a monitor device 12 for receiving the second image; a receiving device 13, a monitor 11 for displaying the first image or the second image; and an image switching device 10. The intra-body indwelling capsule 2 is arranged at the distal end of the inserting unit 5, and the separation from the inserting unit 5 is detected and the separation detection result is transmitted. The receiving device 13 receives the separation detection result. The image switching device 10 receives the first image from the endoscope device 14 and the second image from the monitor device 12, and switches the display image of the monitor 11 from the second image to the first image when receiving the separation detection result from the receiving device 13.

4 Claims, 13 Drawing Sheets

U.S. PATENT DOCUMENTS

| | | |
|---|---|---|
| 2003/0013938 A1 | 1/2003 | Iddan et al. |
| 2003/0023150 A1 | 1/2003 | Yokoi et al. |
| 2004/0133076 A1* | 7/2004 | Kobayashi et al. ........... 600/175 |
| 2005/0165272 A1 | 7/2005 | Okada et al. |
| 2006/0209185 A1 | 9/2006 | Yokoi |

FOREIGN PATENT DOCUMENTS

| | | |
|---|---|---|
| JP | 2001-526072 | 12/2001 |
| JP | 2004-49756 | 2/2004 |
| WO | WO 94/05200 A1 | 3/1994 |
| WO | WO 2005/048825 A1 | 6/2005 |
| WO | WO 2005/053517 A1 | 6/2005 |
| WO | WO 2005/062717 A2 | 7/2005 |

OTHER PUBLICATIONS

Extended Supplementary Partial European Search Report dated Jul. 17, 2012 from related application EP 06768201.3—2319.

* cited by examiner

IN VIVO IMAGING DEVICE, DISPLAY DEVICE, IMAGING AND DISPLAYING SYSTEM AND INTRA-SUBJECT INDWELLING SYSTEM USING THE SAME

TECHNICAL FIELD

The present invention relates to an in vivo imaging device, a display device, and an imaging and displaying system and an intra-subject indwelling system using the same, particularly, to an in vivo imaging device, a display device, and an imaging and displaying system and an intra-subject indwelling system using the same used when inserting an inserting unit of an endoscope detachably attached with an intra-body indwelling capsule endoscope, which serves as one example of an in vivo imaging device having an imaging function, into the subject, and placing the intra-body indwelling capsule endoscope at a desired site in the subject.

BACKGROUND ART

Recently, a swallowable capsule endoscope has been proposed in the field of endoscopes. This capsule endoscope is provided with an imaging function and a wireless communication function. The capsule endoscope moves inside the body cavity, for example, the organs such as stomach and small intestine according to the peristaltic movement thereof, and functions to image the image of the inside of the subject at an interval of 0.5 seconds and the like, and to wirelessly transmit the captured image of the inside of the subject to an external receiving device during the period of after swallowed from the mouth of the subject for observation (examination) until naturally excreted. Doctors, nurses etc. diagnose the subject by displaying the image of the inside of the subject stored in the receiving device on the display.

The system for introducing the capsule endoscope into the subject may be that of introducing the capsule endoscope inside the subject, for example, gastrointestinal duct by detachably arranging the capsule endoscope to the distal end of the inserting unit of the endoscope to be inserted to the subject, and inserting the inserting unit of the endoscope into the subject along with the capsule endoscope (see e.g., Patent Document 1).

An intra-intra-body indwelling capsule endoscope to which a configuration to be placed inside the subject is added is proposed with regards to such capsule endoscope. The intra-body indwelling capsule endoscope is placed at the desired site in the subject by medical clips and the like after being introduced into the subject. The intra-body indwelling capsule endoscope placed in this manner captures the image of the desired site at a predetermined interval and wirelessly transmits the captured image to the external receiving device.
Patent Document 1: PCT National Publication No. 2001-526072

DISCLOSURE OF INVENTION

The endoscope inserted into the subject in the above manner generally incorporates an imaging mechanism in the vicinity of the distal end of the inserting unit, and continuously images the image of the inside of the subject by means of the imaging mechanism. The images of the inside of the subject captured in this manner are continuously displayed on the display device of the endoscope system including the relevant endoscope. Doctors, nurses etc. can easily insert the inserting unit of the endoscope into the subject by operating the inserting unit of the endoscope while visually checking the image of the inside of the subject continuously displayed on the display device.

However, in the conventional system for introducing the above described capsule endoscope into the subject, the visual field of the endoscope is blocked by the intra-body indwelling capsule endoscope arranged at the distal end of the inserting unit, and thus becomes difficult to continuously display on the display device a series of images of the inside of the subject from when the intra-body indwelling capsule endoscope is introduced into the subject until the intra-body indwelling capsule endoscope is placed at the desired site in the subject, whereby introduction and placement of the intra-body indwelling capsule endoscope at the desired site in the subject become difficult.

Problem to be Solved by the Invention

It is an object of the present invention to, in view of the above situations, provide an in vivo imaging device, a display device, and an imaging and displaying system and an intra-subject indwelling system using the same, for continuously displaying on the display device a series of images of the inside of the subject until the intra-body indwelling capsule endoscope is placed at the desired site in the subject, and easily placing the intra-body indwelling capsule endoscope at the desired site of the subject.

Means for Solving Problem

An intra-subject indwelling system according to one aspect of the present invention includes an endoscope device that includes an inserting unit to be inserted into a subject, captures a first image of an inside of the subject from a distal end of the inserting unit, and outputs the captured first image; an intra-body indwelling capsule endoscope that is detachably arranged at the distal end of the inserting unit, detects a separation from the inserting unit, transmits a separation detection result notifying the separation to an outside of the subject, captures a second image of the inside of the subject, and transmits the captured second image to the outside of the subject; an in vitro receiving device that receives one of the separation detection result and the second image transmitted to the outside of the subject, and outputs one of the received separation detection result and the second image; a monitor that displays one of the first image and the second image; and an image switching device that receives the first image and the second image, and switches an image to be displayed on the monitor from the second image to the first image when receiving the separation detection result.

In the intra-subject indwelling system according to the present invention, the image switching device may make the second image an image to be displayed on the monitor for an initial state of the case where the intra-body indwelling capsule endoscope is arranged at the distal end of the inserting unit.

An imaging and displaying system according to another aspect of the present invention includes a capsule endoscope that includes a second imaging unit which captures a second image; an endoscope device that includes an inserting unit to be inserted to an inside of a subject, a retaining unit which detachably retains the capsule endoscope at the inserting unit, and a first imaging unit which captures a first image; and a display device that displays the second image captured by the capsule endoscope in a retention state where the retaining unit retains the capsule endoscope, and displays the first image captured by the endoscope device when receiving a retention release result notifying a release of the retention state.

A display device according to still another aspect of the present invention includes a monitor that displays a first image captured by a first imaging device, and a second image captured by a second imaging device which has an imaging unit, separately from the first imaging device; an in vitro receiving device that receives a command signal for switching an image to be displayed on the monitor from the second image to the first image from one of the first imaging device and the second imaging device; and an image switching device that switches the image to be displayed on the monitor from the second image to the first image when receiving the command signal from the in vitro receiving device.

An in vivo imaging device according to still another aspect of the present invention includes a first imaging unit that captures a first image; and a signal transmitting unit that transmits a command signal notifying to switch an image to be displayed on an external monitor from the first image to a second image captured by a second imaging unit separate from the first imaging unit.

Effect of the Invention

According to the present invention, a series of images of the inside of the subject from when the inserting unit of the endoscope arranged with the intra-body indwelling capsule endoscope at the distal end is inserted to the inside of the subject until the intra-body indwelling capsule endoscope is placed at a desired site in the subject are captured and continuously displayed on the display device, and thus an advantage in that the intra-body indwelling capsule endoscope can be easily introduced and placed at the desired site in the subject is obtained.

EXPLANATIONS OF LETTERS OR NUMERALS 1, 21 INTRA-SUBJECT INDWELLING SYSTEM
2, 22 INTRA-BODY INDWELLING CAPSULE
3, 23 CAPSULE MAIN BODY
3a IMAGING MECHANISM
3b IMAGE PROCESSOR
3c PARAMETER STORAGE UNIT
3d TRANSMITTING UNIT
3e TRANSMITTING ANTENNA
3f, 23f CONTROL UNIT
3g POWER SUPPLY
3m HOUSING
3n TRANSPARENT MEMBER
4, 24 INDWELLING UNIT
4a PRESSURE SENSOR
4b TRANSMITTING UNIT
4c TRANSMITTING ANTENNA
4d CONTROL UNIT
4e POWER SUPPLY
4f MAGNETIC SENSOR
5 INSERTING UNIT
5a, 5b FORCEPS CHANNELS
5c CAP
5d MAGNET
6 IMAGING MECHANISM
7 OPERATION DEVICE
8 LIGHT SOURCE DEVICE
9 IMAGE PROCESSOR
9a CONTROL UNIT
10 IMAGE SWITCHING DEVICE
10a RESET BUTTON
10b SWITCH BUTTON
10c SWITCHING CIRCUIT
10d CONTROL UNIT
11 MONITOR
12, 32 MONITOR DEVICE
12a OPERATING UNIT
12b RECEIVING UNIT
12c DISPLAY UNIT
12d, 32d CONTROL UNIT
13 RECEIVING DEVICE
14 ENDOSCOPE DEVICE
15a CLIP
15b STRING MEMBER
16 RETAINING MEMBER
16a CONVEX PART
16b MAGNET
17 CLIPT OPERATION DEVICE
23h MAGNETIC SENSOR
50 RECEIVING DEVICE
50a RECEIVING ANTENNA
51 RECORDING MEDIUM
100 SUBJECT

A PRESSURE SENSITIVE PART
B OPENING
P OPERATIVE SCAR

BEST MODE(S) FOR CARRYING OUT THE INVENTION

The preferred embodiments of an in vivo imaging device, a display device, an imaging and displaying system and an intra-subject indwelling system using the same will now be described in detail with reference to drawings. It is to be noted that the present invention is not limited to the present embodiment.

First Embodiment

Figure 1:
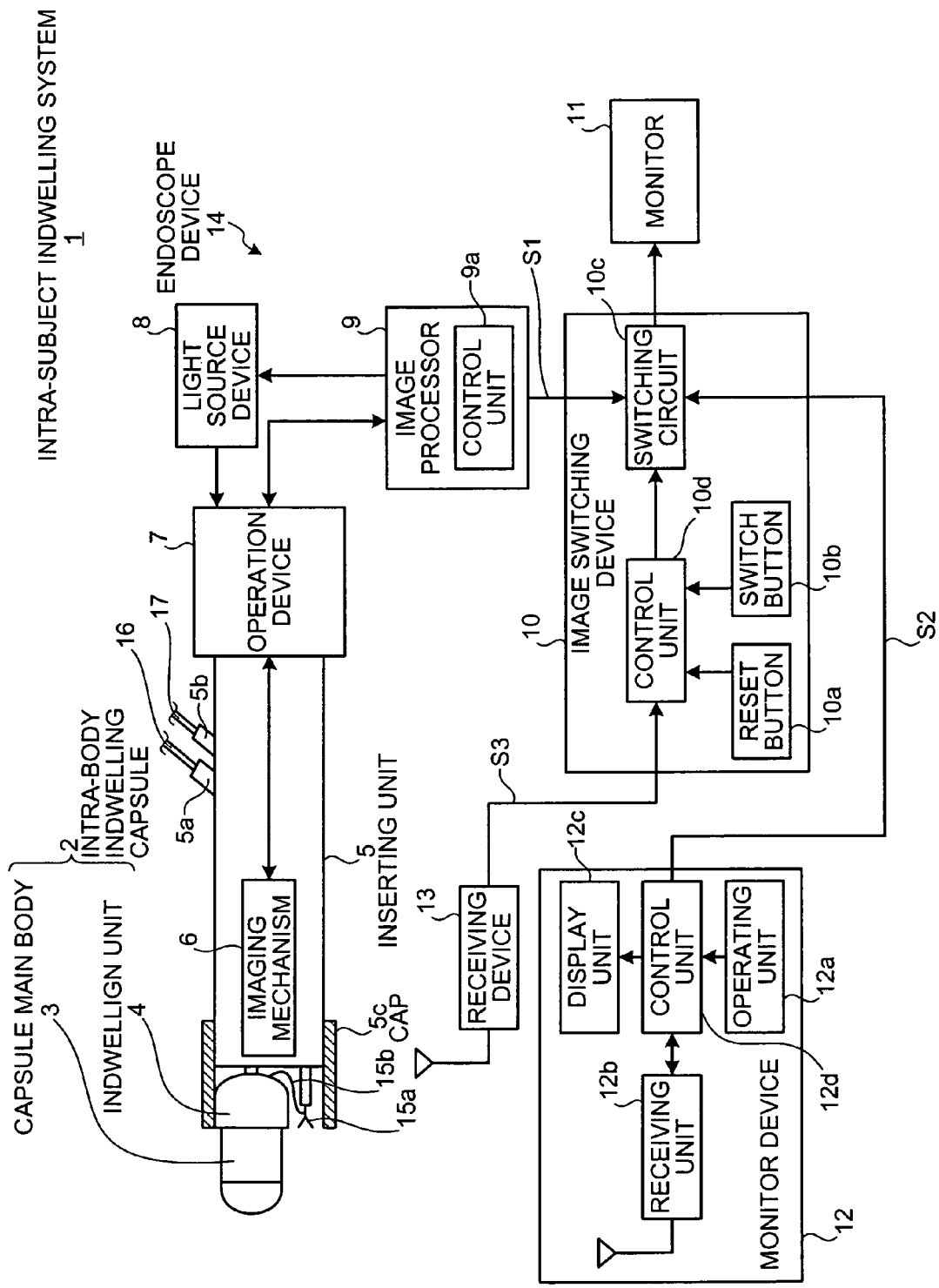
FIG. 1 is a frame format view showing in a frame format one configuration example of an intra-subject indwelling system, which is a first embodiment of the present invention.

FIG. 1 is a frame format view showing in a frame format one configuration example of an intra-subject indwelling system, which is a first embodiment of the present invention. As shown in FIG. 1, the intra-subject indwelling system 1 includes an intra-body indwelling capsule endoscope (hereinafter referred to as intra-body indwelling capsule) 2, placed at a desired site in the subject, for imaging the image of the desired site; and an endoscope device 14 used in introduction and placement of the intra-body indwelling capsule 2 at the desired site of the subject. The intra-subject indwelling system 1 also includes a monitor 11 for displaying the image captured by the endoscope device 14 (hereinafter referred to as endoscope image) or the image captured by the intra-body indwelling capsule 2 (hereinafter referred to as capsule image), and an image switching device 10 for switching the display image of the monitor 11 between the endoscope image and the capsule image. Furthermore, the intra-subject indwelling system 1 includes a monitor device 12 for acquiring the capsule image from the intra-body indwelling capsule 2 and outputting the acquired capsule image to the image switching device 10, and a receiving device 13 for receiving a separation detection result indicating that the intra-body indwelling capsule 2 has separated from the endoscope device 14, and outputting the received separation detection result to the image switching device 10. In this case, the display device of switching and displaying the endoscope image and the capsule image using the relevant monitor 11, the image switching device 10, and the receiving device 13 is realized.

The intra-body indwelling capsule 2 has a function serving as an imaging device for imaging the image of the inside of the subject by being introduced into the subject, serving as one example of an in vivo imaging device. Specifically, the intra-body indwelling capsule 2 is realized using a capsule endoscope main body (hereinafter referred to as capsule main body) 3 including an imaging function and a wireless communication function inside a capsule shaped housing, and a indwelling unit 4 including a device placing the capsule main body 3 at a desired site in the subject. When introduced into the subject, the capsule main body 3 images the image of the inside of the subject at a predetermined interval, for example, at an interval of 0.5 seconds, and transmits a wireless signal containing the captured image, that is, the capsule image to the monitor device 12 exterior to the subject. The indwelling unit 4 is attached to the back end side and the like of the capsule main body 3. The indwelling unit 4 includes a medical clip 15a and a string member 15b as the device for placement. The indwelling unit 4 has a separation detecting function of detecting that the intra-body indwelling capsule 2 arranged at the distal end (specifically, distal end of inserting unit 5 to be hereinafter described) of the endoscope device 14 has separated, and a wireless transmitting function of transmitting the wireless signal containing the separation detection result indicating the relevant separation. In this case, the indwelling unit 4 transmits the wireless signal containing the relevant separation detection result to the receiving device 13 exterior to the subject. The details of the intra-body indwelling capsule 2 will be hereinafter described.

The endoscope device 14 has a function serving as an imaging device for imaging the image of the inside of the subject and is used to introduce the intra-body indwelling capsule 2 into the subject and place the intra-body indwelling capsule 2 at the desired site in the subject. Specifically, the endoscope device 14 includes an inserting unit 5 to be inserted into the subject, an imaging mechanism 6 for imaging the image of the inside of the subject and the like from the distal end of the inserting unit 5, and an operation device 7 for operating the relevant inserting unit 5 and the imaging mechanism 6. The endoscope device 14 further includes a light source device 8 for illuminating the imaging visual field of the imaging mechanism 6, and an image processor 9 for generating the endoscope image based on the image signal from the imaging mechanism 6.

The inserting unit 5 is an elongate tubular member suited for the insertion into the body cavity of the subject and also has flexibility. The inserting unit 5 has the imaging mechanism 6 incorporated in the vicinity of the distal end (side to be inserted into the subject), and the operation device 7 arranged at the basal end. Furthermore, forceps channels 5a, 5b acting as pass through holes for communicating the distal end and the vicinity of the basal are formed inside the inserting unit 5.

A tubular retaining member 16 functioning as a retaining unit for retaining the intra-body indwelling capsule 2 at the distal end of the inserting unit 5 is inserted to the forceps channel 5a. The relevant retaining member 16 has one end detachably attached to the back end of the indwelling unit 4, and the other end exposed from the basal end side of the inserting unit 5. Doctors, nurses etc. thus can detachably retain the intra-body indwelling capsule 2 at the distal end of the inserting unit 5 by gripping the basal end side of the retaining member 16.

A clip operation device 17 for operating the clip 15a is inserted to the forceps channel 5b. Specifically, the clip operation device 17 has a tubular member, which is inserted through the forceps channel 5b. The relevant clip operation device 17 detachably includes the clip 15a at the distal end of the tubular member, and has a clip operation part (not shown) at the basal end of the tubular member. Doctors, nurses etc. thus are able to fasten the clip 15a at the desired site in the subject by operating the clip operation part.

A tubular cap 5c is attached to the outer periphery of the distal end of the inserting unit 5. The cap 5c widens the insertion passage (e.g., alimentary canal etc.) of the subject when the inserting unit 5 arranged with the intra-body indwelling capsule 2 is inserted into the subject, thereby facilitating the introduction of the intra-body indwelling capsule 2. In this case, the cap 5c regulates the orientation of the intra-body indwelling capsule 2 and prevents the retaining member 16 from being bent. The cap 5c also facilitates the discharge of the clip 15a to the desired site of the subject by widening the relevant passage, and prevents the subject from being unintentionally damaged by the clip 15a. The cap 5c is desirably arranged so as not to block the imaging visual field of the imaging mechanism 6, but a transparent member may be used.

The imaging mechanism 6 functions as the imaging part of the endoscope device 14, and images the image of the inside of the subject seen from the distal end of the inserting unit 5. Specifically, the imaging mechanism 6 is achieved using the optical system of lens or the like, and the imaging elements of CCD, CMOS or the like, and has a predetermined imaging visual field that widens towards the outside of the inserting unit 5 from the distal end of the inserting unit 5. When the imaging visual field is illuminated by the light source device 8, the imaging mechanism 6 receives the reflected light from the imaging visual field, and photoelectric transfers the received reflected light. In this manner, the imaging mechanism 6 images the image of the imaging visual field, for example, the image of the inside of the subject, and generates an image signal containing the obtained image data. The relevant image signal is input to the image processor 9 via the inserting unit 5 and the operation device 7.

The operation device 7 performs a curving operation of the inserting unit 5, an imaging operation start or terminating operation by the imaging mechanism 6. Specifically, the operation device 7 is provided with various operation switches etc., and is gripped and operated by doctors etc. when operating the endoscope device 14. For example, doctors etc. can insert the inserting unit 5 into the subject, perform the bending operation of the distal end of the inserting unit 5, and image the images of the inside of the subject by gripping and operate the relevant operation device 7.

The light source device 8 illuminates the imaging visual field of the imaging mechanism 6. Specifically, the light source device 8 outputs the illumination light to the imaging visual field of the imaging mechanism 6 via the operation device 7 and a light guide (not shown) arranged in the inserting unit 5 when the operation switch of the operation device 7 is turned ON, and illuminates the imaging visual field.

The image processor 9 generates the image captured by the imaging mechanism 6, that is, the endoscope image. Specifically, the image processor 9 receives the image signal from the imaging mechanism 6 via the inserting unit 5 and the operation device 7, and performs a predetermined image process on the received image signal to generate the endoscope image. The image processor 9 transmits the generated endoscope image to the image switching device 10 as an endoscope image signal S1. Furthermore, the image processor 9 includes a control unit 9a for controlling the drive of the imaging mechanism 6 and the light source device 8. The control unit 9a performs a control on the light source device 8 to output the light for illuminating the imaging visual field, and in synchronization therewith, performs a control on the imaging mechanism 6 to image the image of the imaging visual field.

The monitor device 12 receives the capsule image from the intra-body indwelling capsule 2 via a predetermined electric wave, and displays on the monitor the received capsule image in real time, serving as one example of an in vitro receiving device. Specifically, the monitor device 12 includes an operating unit 12a for performing various operations of the monitor device 12, a receiving unit 12b including a receiving antenna for receiving the wireless signal output by the capsule main body 3, a display unit 12c for monitor displaying the capsule image, and a control unit 12d for controlling each drive of the operating unit 12a, the receiving unit 12b, and the display unit 12c.

The receiving unit 12b receives the wireless signal from the capsule main body 3 via the predetermined electric wave, performs demodulation process etc. on the received wireless signal, and restores the image signal of the capsule image based on the wireless signal. The receiving unit 12b transmits the restored image signal to the control unit 12d. The control unit 12d is activated in response to the input operation of the operating unit 12a by doctors, nurses, etc., and controls the drive of the operating unit 12a, the receiving unit 12b, and the display unit 12c. In this case, the control unit 12d receives the image signal restored by the receiving unit 12b as described above, performs a predetermined image process on the received image signal, and generates the capsule image based on the image signal. The control unit 12d transmits the capsule image signal containing the relevant capsule image to the display unit 12c, and performs the control of displaying the capsule image on the display unit 12c. The control unit 12d transmits the capsule image signal S2 to the image switching device 10. The display unit 12c displays on the monitor the capsule image based on the capsule image signal received from the control unit 12d.

The receiving device 13 receives the separation detection result of the intra-body indwelling capsule 2 via the predetermined electric wave, and outputs the received separation detection result to the image switching device 10, serving as one example of the in vitro receiving device. Specifically, the receiving device 13 includes a receiving antenna for receiving the wireless signal from the indwelling unit 4 via the predetermined electric wave, and performs demodulation process and the like on the wireless signal received using the receiving antenna and acquires the separation detection result based on the relevant wireless signal. The receiving device 13 transmits the acquired separation detection result to the image switching device 10 as the separation detection signal S3.

The frequency band of the electric wave transmitted and received between the receiving device 13 and the indwelling unit 4 is preferably different from the frequency band of the electric wave transmitted and received between the receiving unit 12b of the above described monitor device 12 and the capsule main body 3, but may be the same.

The monitor 11 displays the above described endoscope image and the capsule image. Specifically, the monitor 11 displays the endoscope image based on the endoscope image signal S1 when receiving the endoscope image signal S1 via the image switching device 10, and displays the capsule image based on the capsule image signal S2 when receiving the capsule image signal S2 via the image switching device 10. Therefore, the monitor 11 switches the display image between the endoscope image or the capsule image as the image signal input via the image switching device 10 is switched.

The image switching device 10 switches the display image of the monitor 11 between the endoscope image and the capsule image described above. Specifically, the image switching device 10 includes a reset button 10a for inputting the instruction (reset instruction) for displaying the capsule image on the monitor 11, a switch button 10b for inputting the instruction (switching instruction) for switching the display image of the monitor 11 to the endoscope image or the capsule image, a switching circuit 10c for switching the image signal to be transmitted to the monitor 11 to the endoscope image signal S1 or the capsule image signal S2, and a control unit 10d for controlling the switching operation of the switching circuit 10c.

The switching circuit 10c receives the endoscope image signal S1 output from the image processor 9 and the capsule image signal S2 output from the control unit 12d of the monitor device 12, performs a switching operation based on the control of the control unit 10d, and transmits the endoscope image signal S1 or the capsule image signal S2 to the monitor 11.

The control unit 10d controls the switching operation of the switching circuit 10c so as to transmit the capsule image signal S2 to the monitor 11 based on the reset instruction input by the reset button 10a. Furthermore, the control unit 10d receives the separation detection signal S3 transmitted by the receiving device 13, and acquires the above described separation detection result based on the separation detection signal S3. In other words, the control unit 10d acquires the separation detection result from the indwelling unit 4 via the receiving device 13, and is notified that the intra-body indwelling capsule 2 has separated from the endoscope device 14 (specifically, distal end of the inserting unit 5) based on the separation detection result. In this case, the control unit 10d controls the switching operation of the switching circuit 10c so as to transmit the endoscope image signal S1 to the monitor 11 when triggered by the acquisition of the relevant separation detection result. In other words, the wireless signal from the indwelling unit 4 corresponding to the separation detection result is a command signal for switching the display image of the monitor 11 from the capsule image to the endoscope image, and is a signal for controlling the control timing of the switching operation of the above described switching circuit 10c. Therefore, the control timing of the switching operation of the above described switching circuit 10c is controlled when the control unit 10d receives the separation detection signal S3 corresponding to such command signal via the receiving device 13.

The control unit 10d performs the control of switching the image signal to be transmitted to the monitor 11 to the endoscope image signal S1 or the capsule image signal S2 each time the switching instruction is input by the switch button lob. In this case, the control unit 10d performs the control of switching the switching circuit 10c from the state of transmitting the endoscope image signal S1 to the state of transmitting the capsule image signal S2 to the monitor 11, or performs the control of switching the switching circuit 10c from the state of transmitting the capsule image signal S2 to the state of transmitting the endoscope image signal S1 to the monitor 11.

The display device for switching and displaying the endoscope image and the capsule image is achieved by combining the monitor 11, the image switching device 10, and the receiving device 13. Such display device functions to display the capsule image in a state (retention state) where the retaining member 16 retains the intra-body indwelling capsule 2 at the distal end of the inserting unit 5, and switching from the capsule image to the endoscope image and displaying the same when receiving the separation detection result indicating that the retention state has been released, or that the intra-body indwelling capsule 2 has separated from the distal end of the inserting unit 5.

Figure 2:
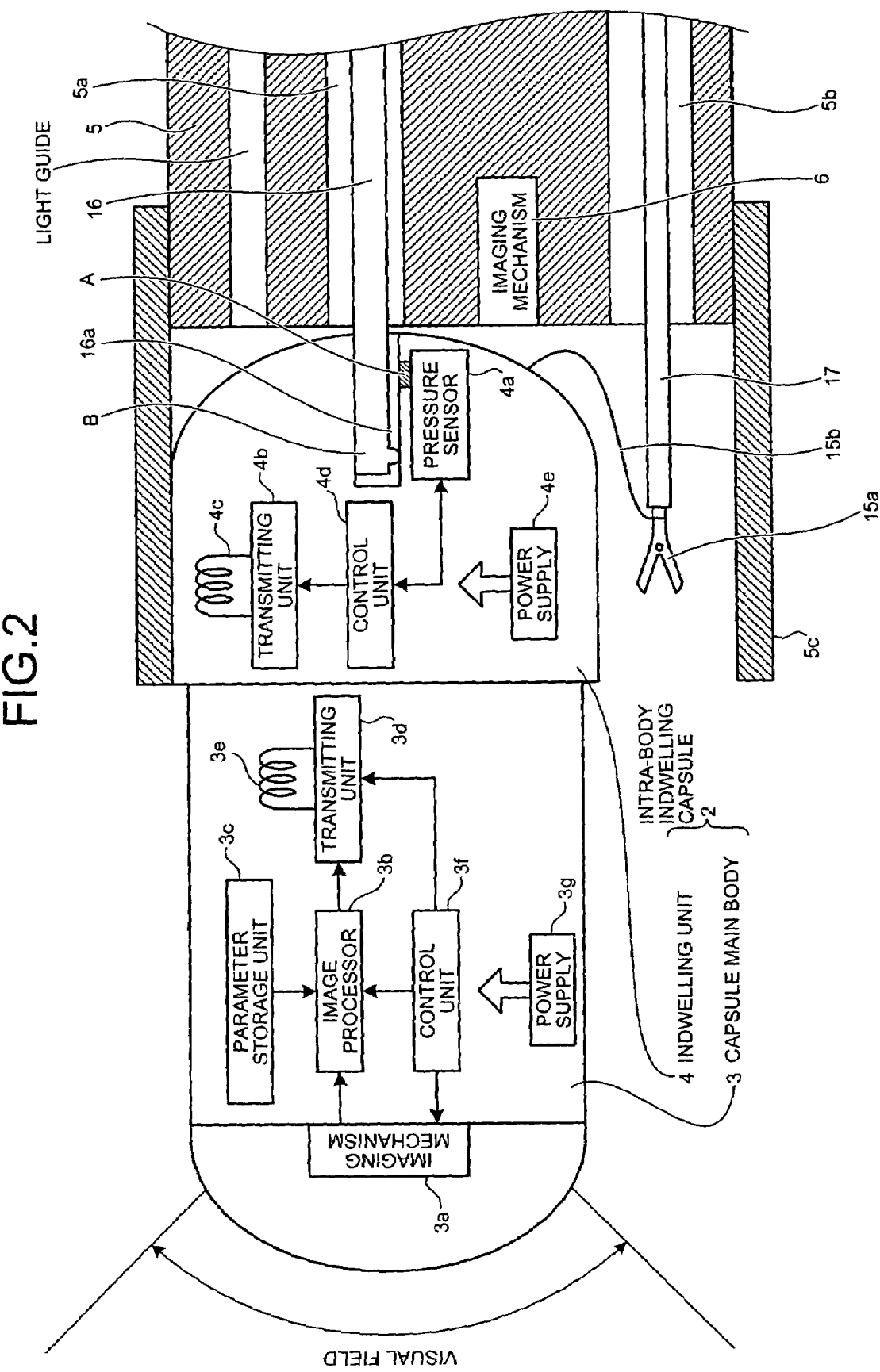
FIG. 2 is a block diagram showing in a frame format one configuration example of the intra-body indwelling capsule of the first embodiment.
Figure 3:
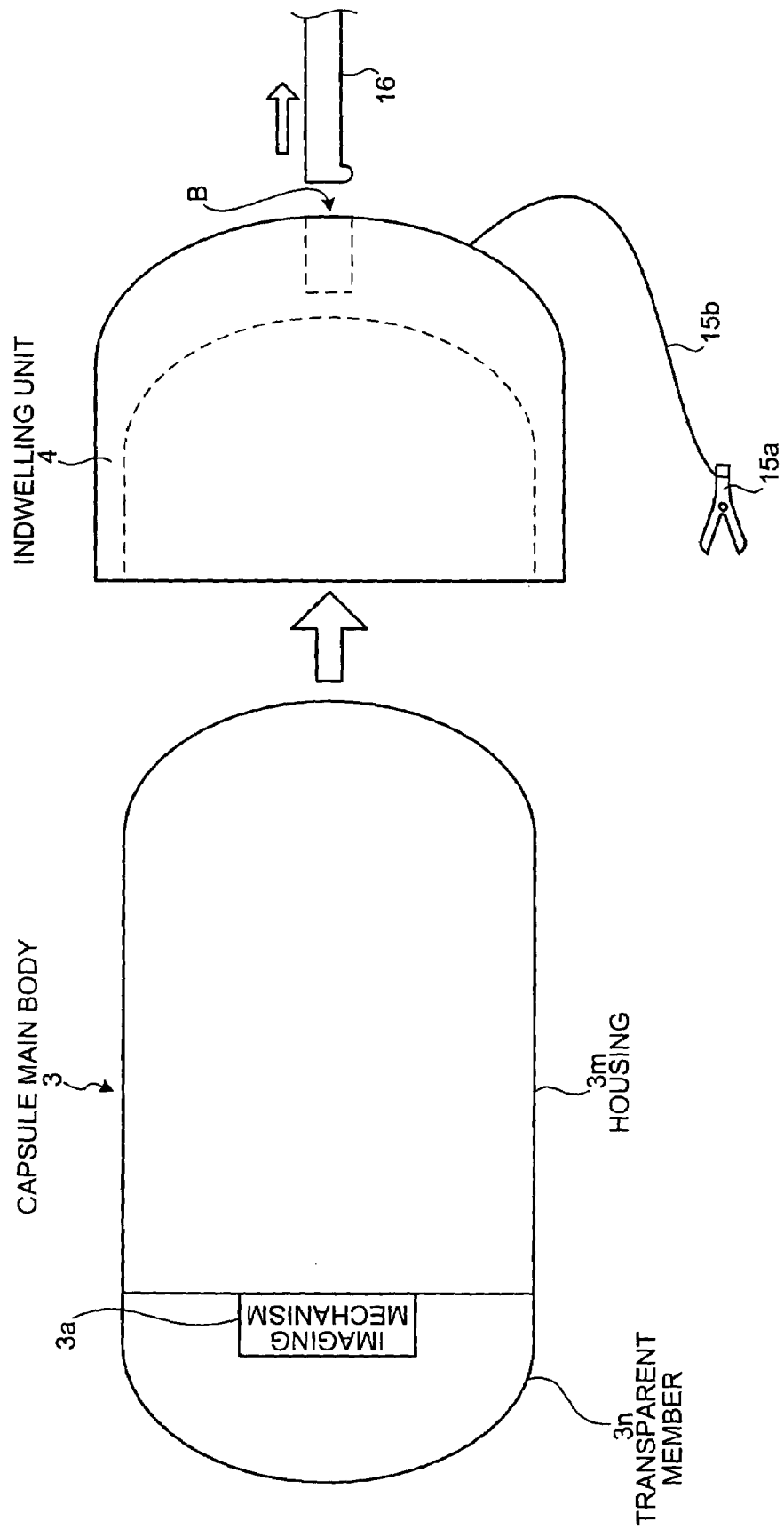
FIG. 3 is a frame format view showing in a frame format a state in which the capsule main body and the indwelling unit are disassembled.

The configuration of the intra-body indwelling capsule 2 will now be described in detail. FIG. 2 is a block diagram showing in a frame format one configuration example of the intra-body indwelling capsule 2. FIG. 3 is a frame format view showing in a frame format the state in which the capsule main body 3 and the indwelling unit 4 are disassembled. In FIG. 2, the intra-body indwelling capsule 2 detachably attached to the distal end of the inserting unit 5 is illustrated.

As shown in FIGS. 2 and 3, the intra-body indwelling capsule 2 is realized using the capsule main body 3 and the indwelling unit 4. The capsule main body 3 has a capsule shaped housing 3m with the transparent member 3n used for the distal end side. The indwelling unit 4 is formed with a concave part for engaging the back end of the relevant housing 3m, and is attached to the back end of the capsule main body 3. The relevant indwelling unit 4 includes the medical clip 15a and the string member 15b as a device for placing the intra-body indwelling capsule 2. The clip 15a is connected to the indwelling unit 4 by way of the string member 15b. The indwelling unit 4 is further formed with an opening B on the back end side, and the retaining member 16 is detachably fitted into the opening B.

The capsule main body 3 includes an imaging mechanism 3a serving as an imaging unit of the capsule main body 3, an image processing section 3b for generating an image signal containing the image captured by the imaging mechanism 3a, and a parameter storage unit 3c for storing parameters such as white balance data (hereinafter referred to a WB data) etc. in advance inside the housing 3m. Furthermore, the capsule main body 3 includes a transmitting unit 3d for generating a wireless signal corresponding to the image signal generated by the image processing section 3b, a transmitting antenna 3e for outputting the wireless signal generated by the transmitting unit 3d to the outside, a control unit 3f for controlling each drive of the imaging mechanism 3a, the image processing section 3b, and the transmitting unit 3d, and a power supply 3g for supplying driving power to each constituting section of the capsule main body 3 inside the housing 3m.

The imaging mechanism 3a has a predetermined imaging visual field widening towards the outside of the capsule main body 3 from the distal end of the housing 3m, and images the image of the relevant imaging visual field, that is, the capsule image. Specifically, the imaging mechanism 3a is realized using a light emitting element such as LED for illuminating the imaging visual field, an optical system such as lens for imaging the reflected light from the imaging visual field illuminated by the light emitting element, and an imaging element such as CCD, CMOS and the like for imaging the image of the imaging visual field based on the reflected light received via the optical system. The imaging mechanism 3a illuminates the imaging visual field through the transparent member 3n of the housing 3m, images the reflected light from the imaging visual field by means of the optical system, and photoelectric converts the reflected light received via the relevant optical system to image the image of the imaging visual field, that is, the capsule image. The imaging mechanism 3a outputs the image data corresponding to the capsule image to the image processing section 3b.

The image processing section 3b generates the image signal corresponding to the capsule image captured by the imaging mechanism 3a. Specifically, the image processing section 3b reads the parameters such as WB data and the like stored in the parameter storage unit 3c, and generates an image signal in which the relevant parameter and the image data corresponding to the capsule image are superimposed when receiving the image data from the imaging mechanism 3a. The image processing section 3b outputs the image signal generated in this manner to the transmitting unit 3d.

The transmitting unit 3d performs a predetermined modulation process, power amplification process and the like on the image signal generated by the image processing section 3b, generates the wireless signal corresponding to the image signal, and transmits the generated wireless signal to the transmitting antenna 3e. The transmitting antenna 3e then transmits the wireless signal input by the transmitting unit 3d to the outside. The wireless signal transmitted in this manner is received by the receiving unit 12b of the monitor device 12 exterior to the subject, as described above.

The control unit 3f controls each drive of the imaging mechanism 3a, the image processing section 3b, and the transmitting unit 3d. In this case, the control unit 3f performs the control of synchronizing the operation timing of illuminating the imaging visual field and the operation timing of imaging the image of the imaging visual field. The control unit 3f further performs a control of driving the imaging mechanism 3a at a predetermined interval, and controls each drive of the image processing section 3b and the transmitting unit 3d so as to sequentially transmit the wireless signal corresponding to the image data output from the imaging mechanism 3a at every predetermined interval.

The indwelling unit 4 incorporates a pressure sensor 4a for detecting the separation of the intra-body indwelling capsule 2 from the inserting unit 5, a transmitting unit 4b and a transmitting antenna 4c for transmitting the separation detection result notifying that the relevant intra-body indwelling capsule 2 has separated from the inserting unit 5 to the outside, a control unit 4d for controlling each drive of the pressure sensor 4a and the transmitting unit 4b, and a power supply 4e for supplying the driving power to the pressure sensor 4a, the transmitting unit 4b, and the control unit 4d.

The pressure sensor 4a detects the separation of the intra-body indwelling capsule 2 from the inserting unit 5. Specifically, the pressure sensor 4a detects the change in pressure produced at the inner wall of the opening B when taking out the retaining member 16 fitted into the opening B of the indwelling unit 4 (i.e., releasing the retention state of the intra-body indwelling capsule 2 by the retaining member 16), and detects the take-out of the retaining member 16 from the indwelling unit 4 based on the change in pressure. For example, the pressure sensor 4a includes a pressure sensitive part A on the inner wall in the vicinity of the opening of the opening B. The pressure sensor 4a detects the change in pressure produced at the pressure sensitive part A as a convex part 16a at the end of the retaining member 16 slidably moves on the pressure sensitive part A when the retaining member 16 is taken out from the opening B, and detects that the retaining member 16 has been taken out from the opening B based on the change in pressure. The intra-body indwelling capsule 2 is retained by the retaining member 16 fitted to the opening B of the indwelling unit 4, as shown in FIG. 2, and is detachably arranged at the distal end of the inserting unit 5 so as to contact the inner wall of the cap 5c. Thus, the intra-body indwelling capsule 2 is released from the retention state at the distal end of the inserting unit 5, and separated from the distal end of the inserting unit 5 when the retaining member 16 is taken out from the indwelling unit 4. In other words, the pressure sensor 4a detects the release of the retention state of the intra-body indwelling capsule 2 and the separation of the intra-body indwelling capsule 2 from the inserting unit 5 by detecting the take-out of the retaining member 16 from the indwelling unit 4 as described above. Therefore, when detecting the take-out of the retaining member 16, the pressure sensor 4a transmits to the control unit 4d the separation detection result notifying that the intra-body indwelling capsule 2 has separated from the distal end of the inserting unit 5. The separation detection result may indicate the separation itself of the intra-body indwelling capsule 2 from the distal end of the inserting unit 5, or may indicate the release of the retention state of the intra-body indwelling capsule 2 for separation (retention release result).

The control unit 4d controls the drive of the pressure sensor 4a, and receives the above described separation detection result from the pressure sensor 4a when the intra-body indwelling capsule 2 is released from the retention state and separated from the inserting unit 5 by the take-out of the retaining member 16. When receiving the separation detection result, the control unit 4d outputs the received separation detection result to the transmitting unit 4b, and performs the control on the transmitting unit 4b to transmit the wireless signal corresponding to the separation detection result to the outside.

The transmitting unit 4b generates the wireless signal containing the separation detection result input by the control unit 4d, and outputs the generated wireless signal to the transmitting antenna 4c. In this case, the transmitting antenna 4c outputs the wireless signal input by the transmitting unit 4b to the outside. The wireless signal output in this manner is received at the receiving device 13 exterior to the subject, as described above. Thereafter, the receiving device 13 transmits the separation detection result based on the wireless signal to the control unit 10d of the image switching device 10 as the separation detection signal S3. In this case, the control unit 10d acquires the detection result notifying that the retention state of the intra-body indwelling capsule 2 is released or is separated based on the separation detection signal S3 and controls the switching operation of the switching circuit 10c at the timing the detection result is acquired. Therefore, the transmitting unit 4b and the transmitting antenna 4c function as a signal transmitting unit of transmitting the control signal for controlling the control timing of the switching operation of the switching circuit 10c, that is, the command signal of switching the display image of the monitor 11 from the capsule image to the endoscope image with respect to the control unit 10d.

The intra-subject indwelling system 1 having the above configuration includes the intra-body indwelling capsule 2, the endoscope device 14, and the display device formed by combining the monitor 11, the image switching device 10 and the receiving device 13, and thus has a function serving as an imaging and displaying system of imaging the image of the inside of the subject by the intra-body indwelling capsule 2 or the endoscope device 14, and switching and displaying the captured image of the inside of the subject, that is, the capsule image and the endoscope image on the monitor 11 of the display device. The intra-subject indwelling system 1 has a function serving as the imaging and displaying system even if the capsule endoscope not equipped with the device for placement in the subject is arranged in place of the intra-body indwelling capsule 2.

Figure 4:
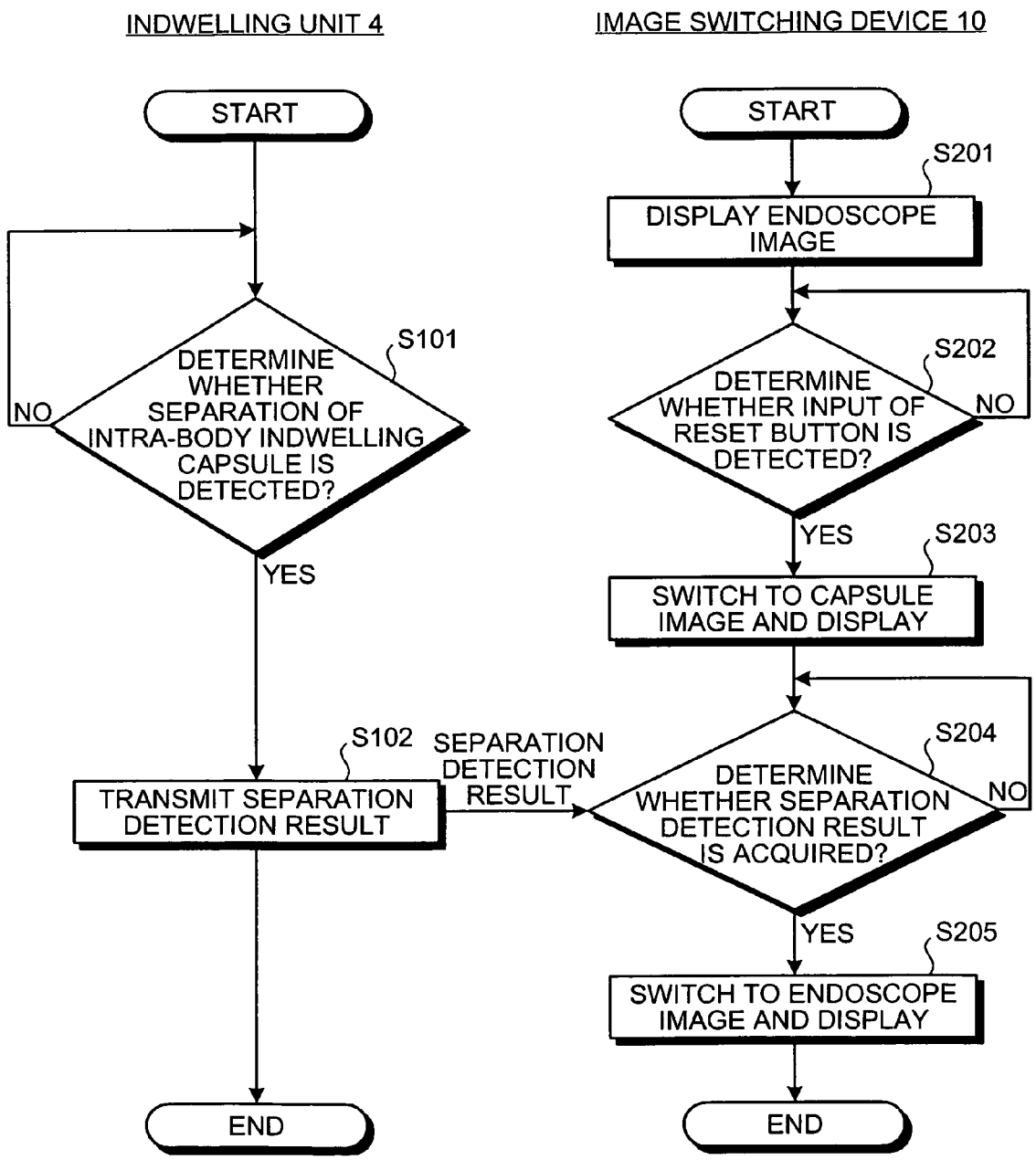
FIG. 4 is a flow chart illustrating the processing procedures of switching the display image of the display device from a capsule image to an endoscope image before and after the separation of the intra-body indwelling capsule.

The operation of the image switching device 10 of switching the display image of the monitor 11 when the intra-body indwelling capsule 2 is separated from the distal end of the inserting unit 5 will now be described. FIG. 4 is a flow chart illustrating the processing procedures of switching the display image of the monitor 11 from the capsule image to the endoscope image when the indwelling unit 4 detects the separation of the intra-body indwelling capsule 2.

As shown in FIG. 4, the image switching device 10 first performs the control of displaying the endoscope image on the monitor 11 (step S201). This is normally for the monitor 11 to function to display the image of the inside of the subject, that is, the endoscope image captured with the endoscope device 14 inserted into the subject, and to display the image visually recognized by doctors, nurses and the like when inserting the endoscope device 14 into the subject and when observing (examining) the inside of the subject. Specifically, in step S201, the control unit 10d performs the control on the switching circuit 10c to transmit the endoscope image signal S1 to the monitor 11. The switching circuit 10c transmits the endoscope image signal S1 received from the image processor 9 to the monitor 11 based on the control of the relevant control unit 10d, and the monitor 11 displays the endoscope image based on the endoscope image signal S1 received in this manner.

The image switching device 10 then monitors the presence of the information input by the input operation of the reset button 10a (step S202), and when the reset instruction input by the reset button 10a is detected (Yes in step S202), switches the display image of the monitor 11 to the capsule image (step S203). In this case, the control unit 10d performs the control on the switching circuit 10c to switch the image signal to be transmitted to the monitor 11 from the endoscope image signal S1 to the capsule image signal S2 with the input of the reset instruction by the reset button 10a as the trigger. The switching circuit 10c transmits the capsule image signal S2 in place of the endoscope image signal S1 on the monitor 11 based on the control of the relevant control unit 10d. The monitor 11 switches from the capsule image to the endoscope image and displays the endoscope image based on the received capsule image signal S2. At this point, the intra-body indwelling capsule 2 is detachably retained at the distal end of the inserting unit 5, as described above. Therefore, the monitor 11 displays the capsule image by the intra-body indwelling capsule 2 as the initial state of when the intra-body indwelling capsule 2 is arranged at the distal end of the inserting unit 5. Doctors, nurses, etc. can then observe the insertion path of the endoscope device 14 inserted into the subject, and easily insert the inserting unit 5 of the endoscope device 14 into the subject with the intra-body indwelling capsule 2 by visually recognizing the capsule image displayed on the monitor 11.

Subsequently, the image switching device 10 monitors the presence of the separation detection result acquired from the intra-body indwelling capsule 2 via the receiving device 13, for example, the separation detection result notifying that the intra-body indwelling capsule 2 has separated from the endoscope device 14 (specifically, inserting unit 5) (step S204), and the processing procedures of step S204 are repeated if the relevant separation detection result is not received (step S204, No). The image switching device 10 repeats the processing procedures of step S202 if the reset instruction is not detected in step S202 (step S202, No).

The intra-body indwelling capsule 2 is detachably arranged at the distal end of the inserting unit 5 of the endoscope device 14, as described above. The indwelling unit 4 of the intra-body indwelling capsule 2 monitors whether or not the intra-body indwelling capsule 2 has separated from the inserting unit 5 (step S101). When detecting the separation of the intra-body indwelling capsule 2 from the relevant inserting unit 5 (step S101, YES), the indwelling unit 4 transmits the wireless signal containing the separation detection result to the receiving device 13 (step S102). Specifically, the control unit 4d detects the take-out of the retaining member 16 using the pressure sensor 4a to detect the retention state release or the separation of the intra-body indwelling capsule 2, and performs the control on the transmitting unit 4b to transmit the wireless signal containing the separation detection result. The separation detection result transmitted by the indwelling unit 4 is received by the receiving device 13, as described above, and input to the image switching device 10 via the receiving device 13. The indwelling unit 4 repeats the processing procedure of step S101 if the separation of the intra-body indwelling capsule 2 is not detected (step S101, No).

When receiving the separation detection result from the indwelling unit 4 via the receiving device 13, as described above (step 104, Yes), the image switching device 10 switches the display image of the monitor 11 to the endoscope image (step S205). Specifically, the control unit 10d receives the separation detection result of the above described intra-body indwelling capsule 2 as the separation detection signal S3 from the receiving device 13, and performs the control on the switching circuit 10c to switch the image signal to be transmitted to the monitor 11 from the capsule image signal S2 to the endoscope image signal S1 with the reception of the separation detection result via the receiving device 13 as the trigger. The switching circuit 10c transmits the endoscope image signal S1 in place of the capsule image signal S2 to the monitor 11 based on the control of the control unit 10d. The monitor 11 switches to the endoscope image from the capsule image, and displays the same based on the received endoscope image signal S1.

In this case, the monitor 11 displays the endoscope image by the endoscope device 14 after separation of the intra-body indwelling capsule 2 in continuation to the capsule image by the intra-body indwelling capsule 2 arranged at the distal end of the inserting unit 5. Thus, doctors, nurses, etc. are able to check the insertion path in the subject by visually checking the capsule image displayed on the monitor 11 while the inserting unit 5 with the intra-body indwelling capsule 2 arranged at the distal end inserted in the subject, and check the inside of the subject and the separated intra-body indwelling capsule 2 by visually checking the endoscope image displayed on the monitor 11 in place of the relevant capsule image after the intra-body indwelling capsule 2 is separated from the inserting unit 5.

Figure 5:
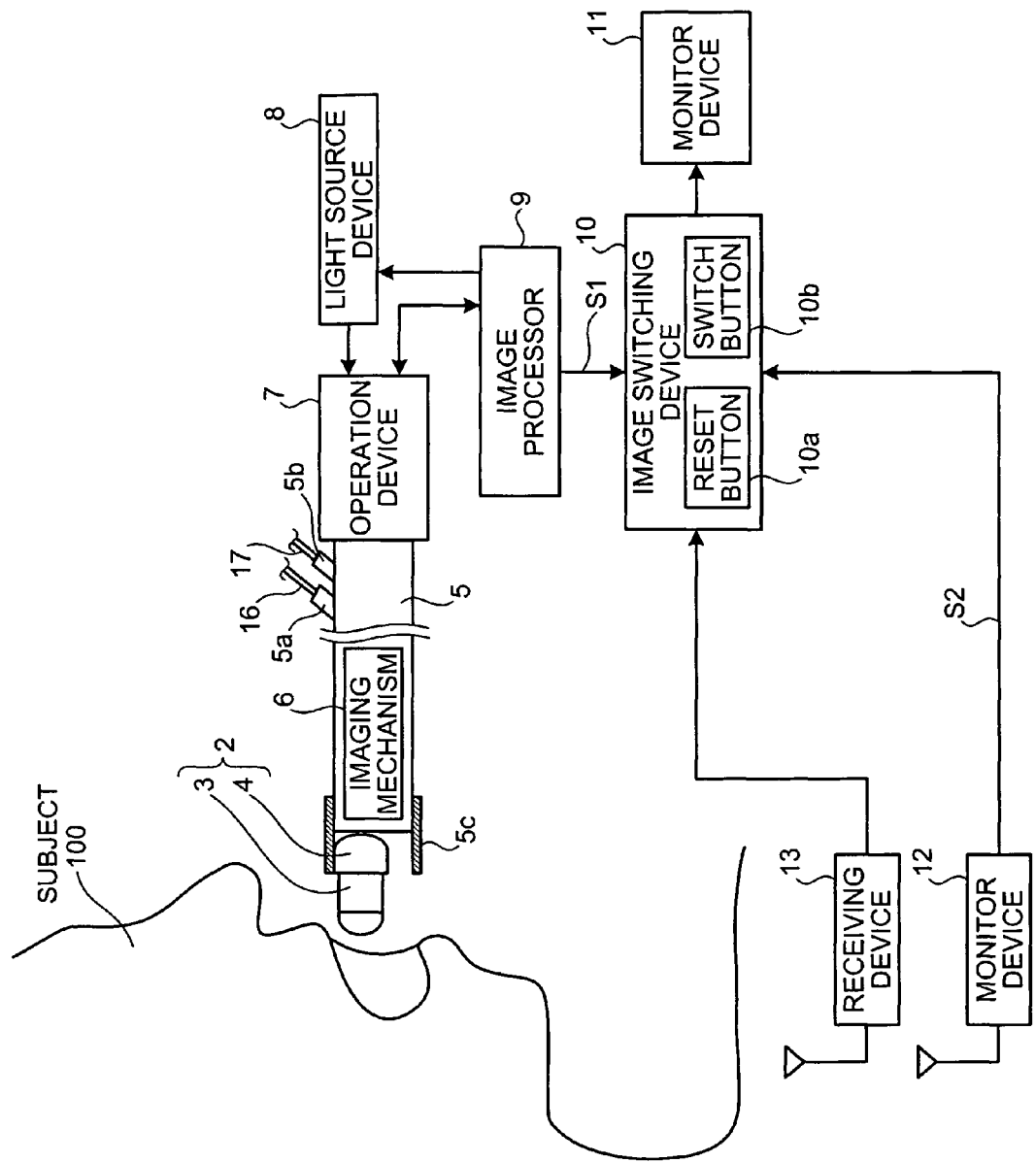
FIG. 5 is a frame format view illustrating the state of introducing the intra-body indwelling capsule arranged at the distal end of the inserting unit into the subject.
Figure 6:
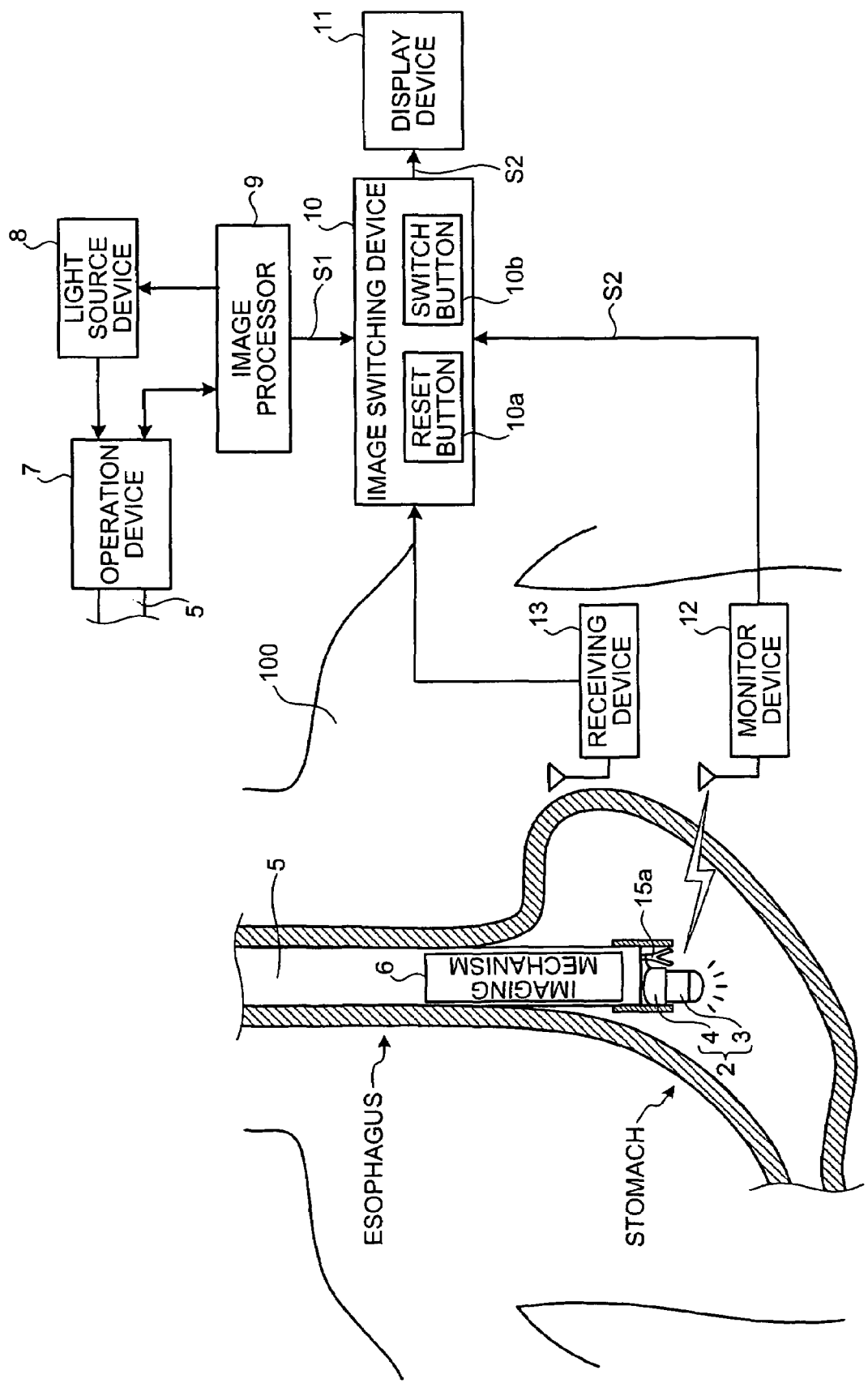
FIG. 6 is a frame format view illustrating the state in which the intra-body indwelling capsule is introduced to the desired site of the subject.
Figure 7:
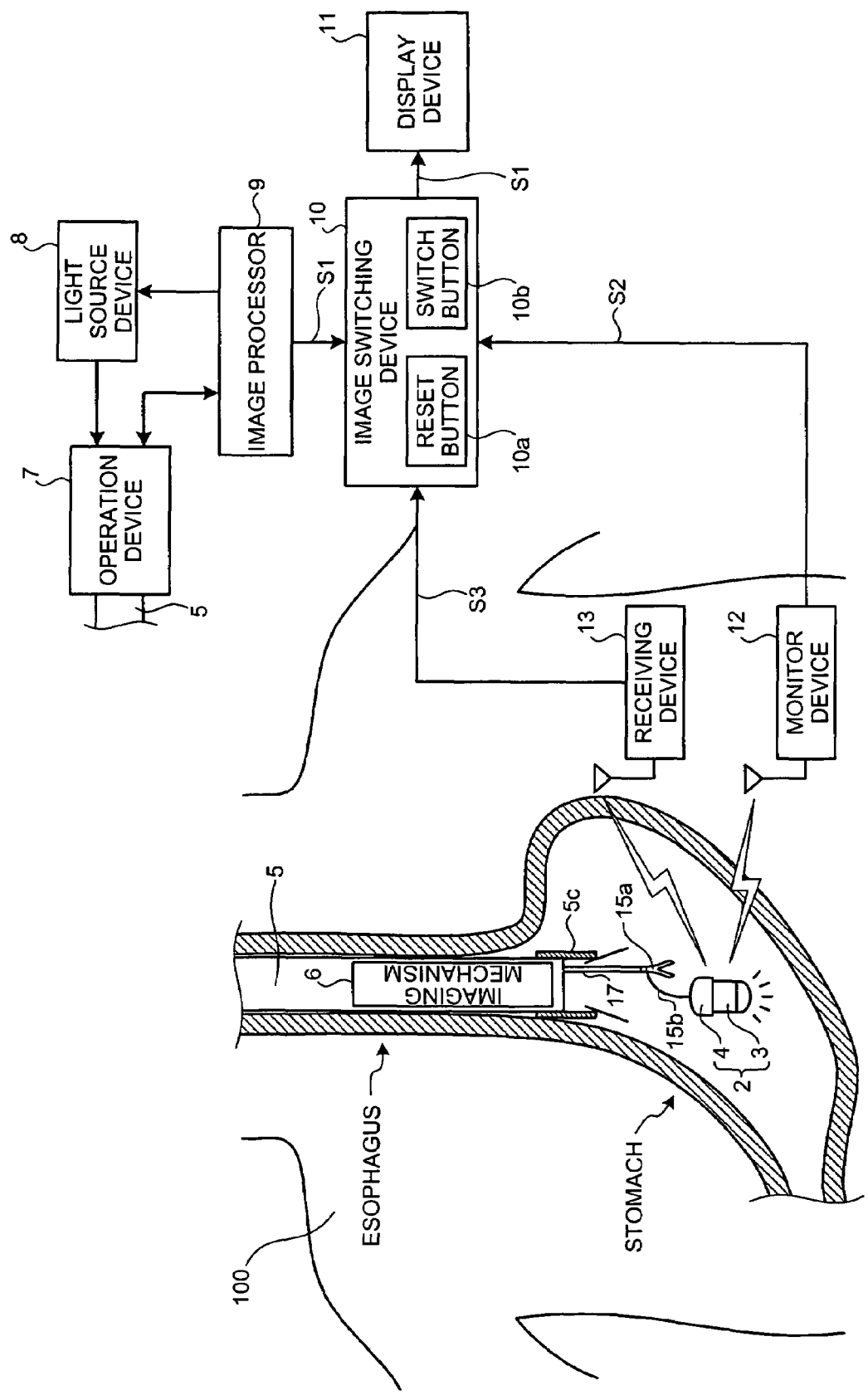
FIG. 7 is a frame format view illustrating the state in which the intra-body indwelling capsule is separated from the inserting unit.

The operation of the image switching device 10 of switching the display image of the monitor 11 will now be described by illustrating the case of introduction and placement of the intra-body indwelling capsule 2 to a desired site, for example, the stomach in the subject. FIG. 5 is a frame format view illustrating the state of introducing the intra-body indwelling capsule 2 arranged at the distal end of the inserting unit 5 into the subject. FIG. 6 is a frame format view illustrating the state in which the intra-body indwelling capsule 2 is introduced to the desired site of the subject. FIG. 7 is a frame format view illustrating the state in which the intra-body indwelling capsule 2 is separated from the inserting unit 5.

As shown in FIG. 5, the intra-body indwelling capsule 2 is detachably arranged at the distal end of the inserting unit 5 using the retaining member 16 and introduced from the mouth of the subject 100 to be placed at the stomach of the subject 100 and the like. In such state, doctors, nurses etc. perform the input operation of the above described reset instruction using the reset button 10a of the image switching device 10. In this case, the image switching device 10 switches the display image of the monitor 11 to the capsule image with the reset instruction as the trigger. In this case, the monitor 11 displays the relevant capsule image as the initial state of when the intra-body indwelling capsule 2 is arranged at the distal end of the inserting unit 5. Doctors, nurses, etc. can check the image in the insertion direction of the inserting unit 5, that is, the insertion path in the subject by visually checking the capsule image displayed on the monitor 11 by the operation of the image switching device 10, and introduce the inserting unit 5 into the subject 100 and insert the intra-body indwelling capsule 2 while visually checking the relevant capsule image.

The intra-body indwelling capsule 2 reaches the stomach of the subject 100 with the inserting unit 5 by the insertion operation of doctors, nurses, etc., as shown in FIG. 6. Until then, the intra-body indwelling capsule 2 sequentially transmits, in a wireless manner, the capsule image of the inside of the subject captured at a predetermined interval to the monitor device 12. The image switching device 10 sequentially receives the capsule image signal S2 from the monitor device 12 as the capsule image, and transmits the received capsule image signal S2 to the monitor 11. The monitor 11 sequentially displays the capsule image indicating the insertion path up to the stomach of the subject 100 based on the relevant capsule image signal S2. Doctors, nurses, etc. can easily introduce the intra-body indwelling capsule 2 to the stomach of the subject 100 by performing the insertion operation of the inserting unit 5 while visually checking the capsule image of the monitor 11.

The intra-body indwelling capsule 2 that has reached the stomach of the subject 100 has the retaining member 16 taken out from the indwelling unit 4 by the take-out operation of the retaining member 16 by doctors, nurses, etc. In this case, the intra-body indwelling capsule 2 separates from the distal end of the inserting unit 5, as shown in FIG. 7. At substantially the same time, the indwelling unit 4 detects the take-out of the relevant retaining member 16, whereby separation of the intra-body indwelling capsule 2 from the inserting unit 5 is detected. The indwelling unit 4 wirelessly transmits the separation detection result of the relevant intra-body indwelling capsule 2 to the receiving device 13. In this case, the image switching device 10 receives the separation detection signal S3 from the receiving device 13 as the separation detection result, and switches the display image of the monitor 11 from the capsule image to the endoscope image with the separation detection result as the trigger. The monitor 11 receives the endoscope image signal S1 in place of the above described capsule image signal S2 by the operation of the image switching device 10, and displays the endoscope image based on the relevant endoscope image signal S1. Specifically, the monitor 11 displays the endoscope image captured including the stomach of the subject 100 and the separated intra-body indwelling capsule 2 in continuation to the capsule image by the intra-body indwelling capsule 2 immediately before being separated from the inserting unit 5.

The separated intra-body indwelling capsule 2 is visually checked in the endoscope image displayed on the monitor 11, and the intra-body indwelling capsule 2 is easily placed in the stomach of the subject 100 by operating the clip operation device 17 while visually checking the relevant endoscope image. The intra-body indwelling capsule 2 wirelessly transmits the capsule image captured at a predetermined interval to the monitor device 12 even after being separated from the inserting unit 5. The image switching device 10 switches the display image of the monitor 11 to the capsule image or the endoscope image each time the switching instruction is input by the switch button 10*b*. Doctors, nurses, etc. are then able to switch the display image of the monitor 11 to the capsule image or the endoscope image as necessary and display the same. For example, doctors etc. are able to perform the operation of placing the intra-body indwelling capsule 2 in the stomach of the subject 100 while visually checking the endoscope image, and adjust the position of the placed intra-body indwelling capsule 2 while visually checking the capsule image switched by operating the switch button 10*b*. The intra-body indwelling capsule 2 is thereby adjusted and placed so as to reliably capture, for example, the affected area or the operative scar of the stomach in the desired observation position or the imaging visual field of the subject 100. The capsule image by the intra-body indwelling capsule 2 after separated from the inserting unit 5 may also be displayed on the monitor device 12.

The clip operation device 17 may be operated with such intra-body indwelling capsule 2 arranged at the distal end of the inserting unit 5, and the clip 15*a* may be attached to the desired site of the subject 100 while visually checking the capsule image captured in such state, and thereafter, the retaining member 16 may be taken out to separate the intra-body indwelling capsule 2 from the inserting unit 5.

Figure 8:
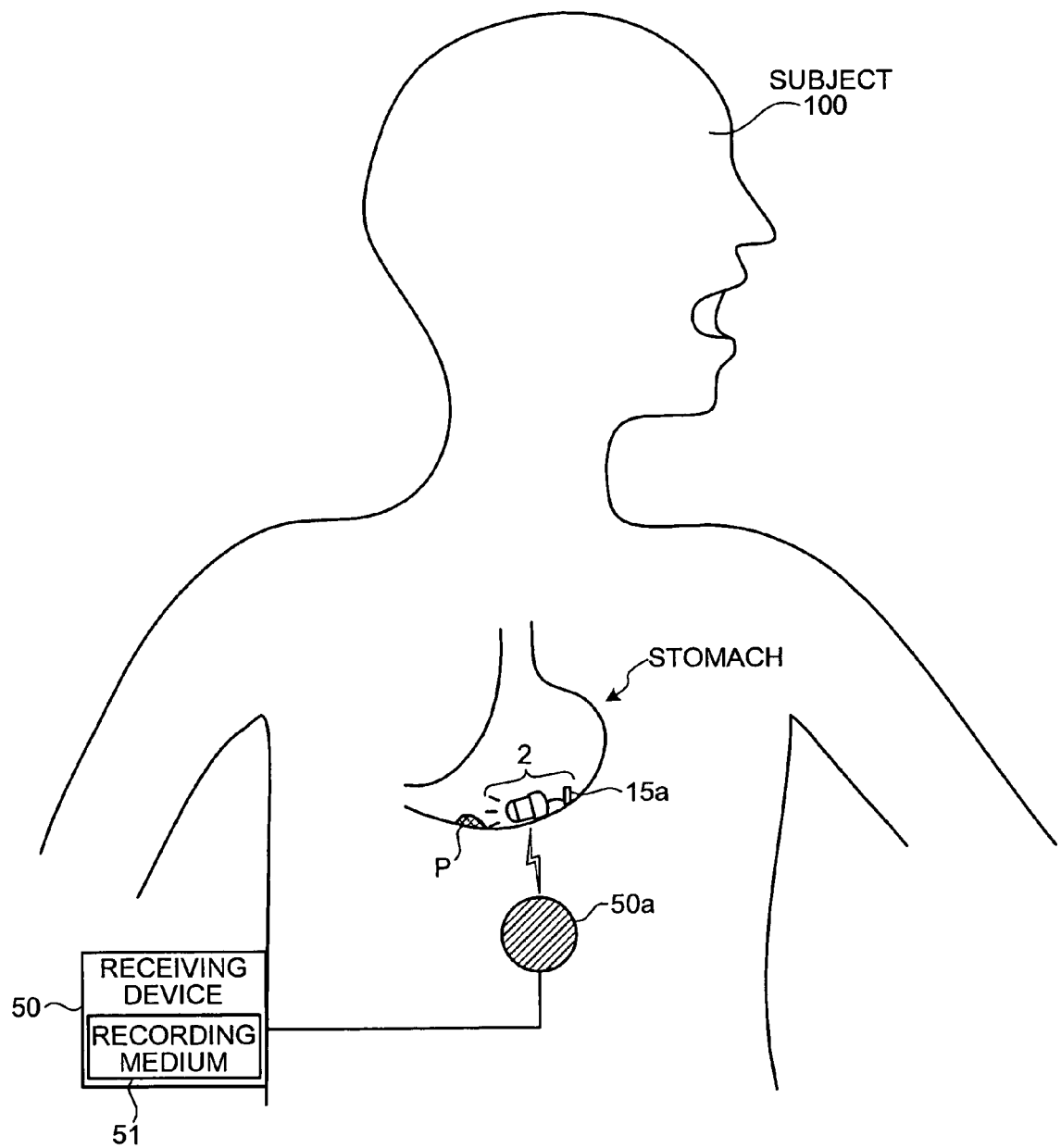
FIG. 8 is a frame format view illustrating the state of sequentially receiving the capsule image captured by the intra-body indwelling capsule placed at the desired site of the subject at the external receiving device.

The intra-body indwelling capsule 2 placed at the desired site (e.g., stomach) of the subject 100 sequentially captures the image of the desired image at a predetermined interval, and sequentially transmits the wireless signal containing the captured image of the desired site, that is, the capsule image to the outside. FIG. 8 is a frame format view illustrating the state of sequentially receiving the capsule image captured by the intra-body indwelling capsule 2 placed at the desired site of the subject 100 in the external receiving device.

As shown in FIG. 8, the receiving device 50, carried by the subject 100, is for sequentially accumulating the capsule image captured by the intra-body indwelling capsule 2. Specifically, the receiving device 50 includes a receiving antenna 50, or a loop antenna and the like, and is detachably attached with a portable recording medium 51. The receiving antenna 50*a* is arranged on the body surface in the vicinity of the intra-body indwelling capsule 2 in the subject 100.

The intra-body indwelling capsule 2 inside the subject 100 images the image of the desired site, for example, the operative scar P at a predetermined interval, and transmits the wireless signal containing the captured image of the operative scar P (i.e., capsule image) to the outside. The receiving device 50 receives the wireless signal from the intra-body indwelling capsule (specifically, capsule main body 3) via the receiving antenna 50*a*, restores the image signal by performing a predetermined demodulation process and the like on the wireless signal, and generates a capsule image based on the image signal. The receiving device 50 sequentially accumulates the generated capsule image in the recording medium 51. Doctors, nurses, etc. attach the recording medium 51 in which the capsule image has accumulated to the image display device of a work station and the like having a predetermined image processing function, and reproduce the capsule image to observe (examine) the operative scar P of the subject 100 and the like. The capsule image accumulated in the receiving device 50 may be reproduced using the above described monitor device 12. In this case, the receiving device 50 is connected to the monitor device 12 by way of a cable and the like, and sequentially transmits the capsule image received via the receiving antenna 50*a* to the monitor device 12. The receiving device 50 and the above described receiving device 13 (see FIG. 1) may be configured as the same device, or as different devices. For example, a receiving device having the function of the receiving devices 13, 50 may be used.

Figure 9:
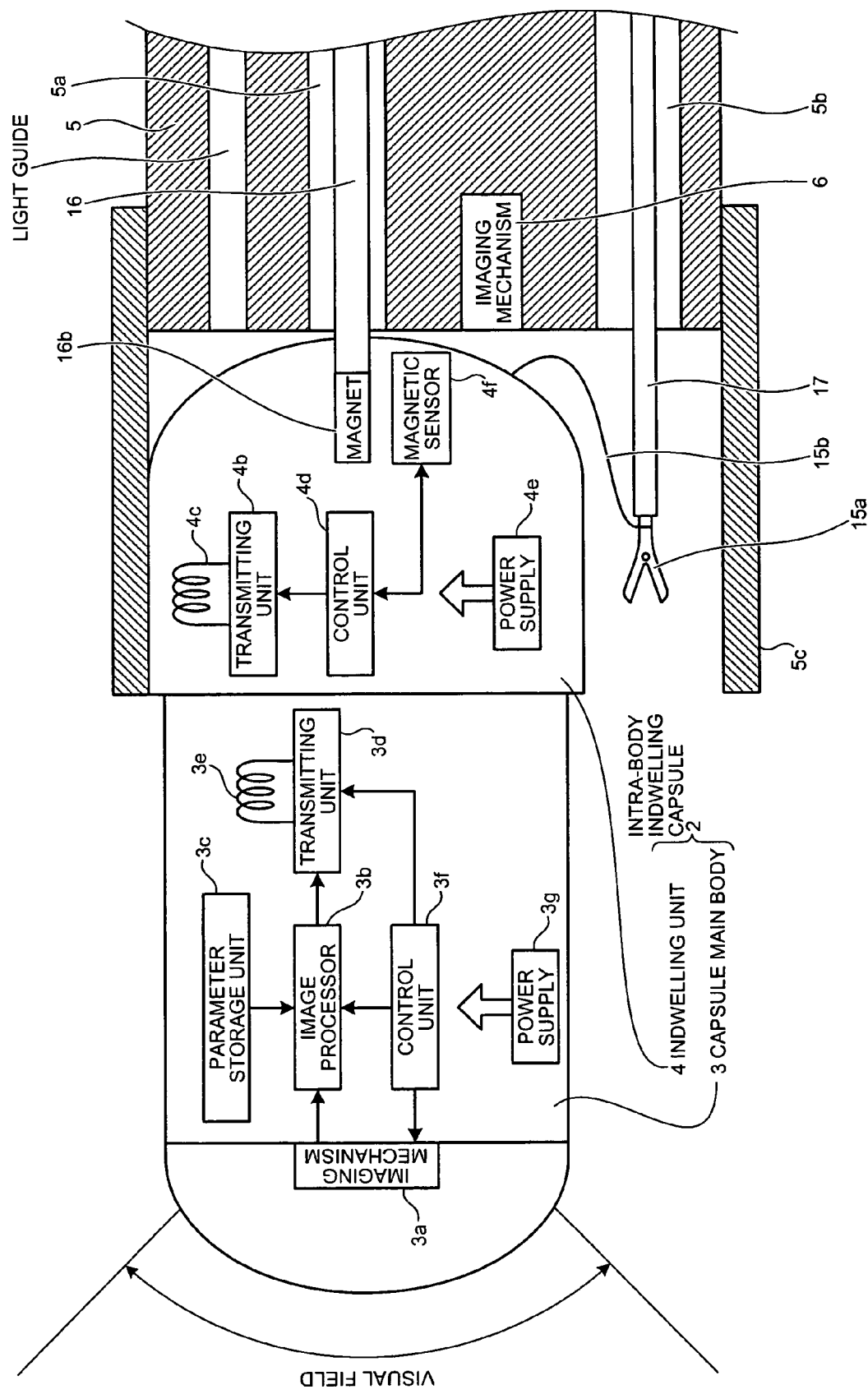
FIG. 9 is a block diagram showing in a frame format a variant of the intra-body indwelling capsule of the first embodiment.

In the first embodiment of the present invention, the take-out of the retaining member 16 has been detected based on the change in pressure that occurs at the inner wall of the opening B when taking out the retaining member 16 from the indwelling unit 4, but the present invention is not limited thereto, and a magnet may be arranged at the distal end of the retaining member 16, and the take-out of the retaining member 16 may be detected based on the change in strength of the magnetism that occurs when taking out the relevant retaining member 16. Specifically, the indwelling unit 4 includes a magnetic sensor 4*f* in the vicinity of the opening B in place of the pressure sensor 4*a*, as shown in FIG. 9. The magnetic sensor 4*f* detects the magnetic strength by the magnet 16*b* arranged at the distal end of the retaining member 16, and detects the take-out of the retaining member 16 based on the decreasing change of the magnetic strength that occurs when the retaining member 16 is taken out. The magnetic sensor 4*f* detects the retention state release or the separation of the intra-body indwelling capsule 2 by detecting the take-out of the retaining member 16. In this case, the control unit 4*d* receives the separation detection result of the intra-body indwelling capsule 2 from the magnetic sensor 4*f*.

Figure 10:
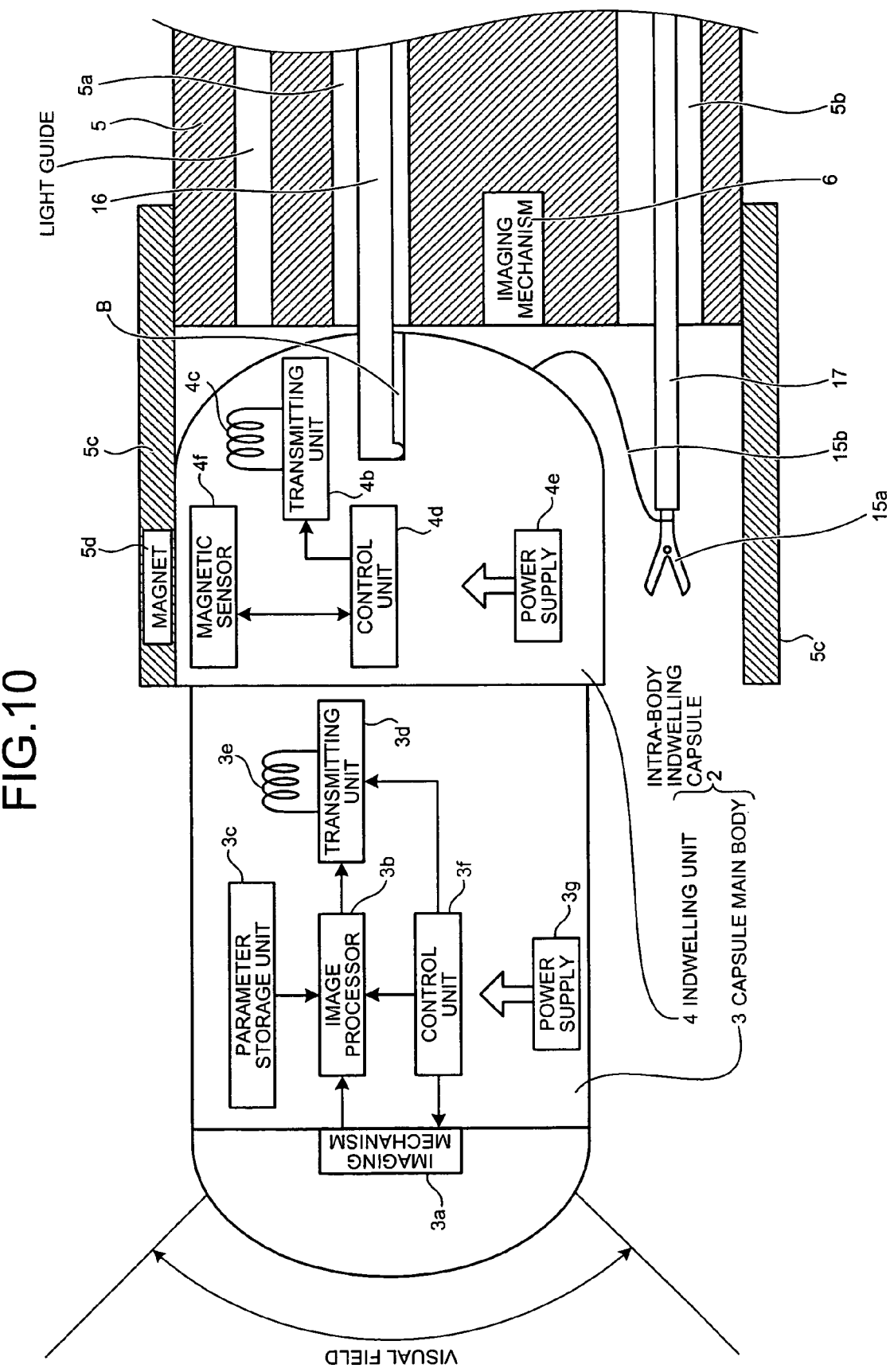
FIG. 10 is a block diagram showing in a frame format another variant of the intra-body indwelling capsule of the first embodiment.

In the first embodiment of the present invention, the separation of the intra-body indwelling capsule 2 has been detected by detecting the take-out of the retaining member 16 from the indwelling unit 4, but the present invention is not limited thereto, and the separation of the intra-body indwelling capsule 2 may be detected by detecting that the indwelling unit 4 has separated from the distal end of the inserting unit 5 by greater than or equal to a predetermined distance. Specifically, as shown in FIG. 10, the magnet 5d is arranged at the cap 5c of the distal end of the inserting unit 5, and the magnetic sensor 4f may be arranged in place of the pressure sensor 4a in the indwelling unit 4 on the side contacting the cap 5c. The magnetic sensor 4f detects the change in strength of the magnetism by the magnet 5d, and detects that the indwelling unit 4 has separated from the inserting unit by greater than or equal to a predetermined distance based on the decreasing change in the magnetic strength that occurs when the distance between the indwelling unit 4 and the distal end (specifically, magnet 5d) of the inserting unit 5 is separated by greater than or equal to a predetermined value. The magnetic sensor 4f detects the separation of the intra-body indwelling capsule 2 by detecting the separation of the indwelling unit 4 and the inserting unit 5. In this case, the control unit 4d receives the separation detection result of the intra-body indwelling capsule 2 from the magnetic sensor 4f.

Furthermore, the endoscope device 14 formed with two forceps channels is used in the first embodiment of the invention, but the present invention is not limited thereto, and an endoscope formed with one or more forceps channel may be applied.

In the first embodiment of the present invention, the capsule image is transmitted and received between the capsule main body 3 and the monitor device 12, and the separation detection result of the intra-body indwelling capsule 2 is transmitted and received between the indwelling unit 4 and the receiving device 13, but the present invention is not limited thereto, and the capsule image and the separation detection result may be transmitted to the monitor device 12. In this case, the receiving unit 12b of the monitor device 12 receives the wireless signal containing the relevant capsule image or the separation detection result, and the control unit 12d extracts or generates the capsule image or the separation detection result based on the signal input from the receiving unit 12b.

The function (separation detecting and transmitting function) of detecting the retention state release or the separation of the intra-body indwelling capsule 2 and wirelessly transmitting the separation detection result is arranged on the intra-body indwelling capsule 2 side (specifically, indwelling unit 4) in the first embodiment of the present invention, but the present invention is not limited thereto, and such separation detecting and transmitting function may be incorporated on the endoscope device 14 side, that is, in the vicinity of the distal end of the inserting unit 5. In this case, the endoscope device 14 having the separation detecting and transmitting function includes the imaging mechanism 6 for imaging the endoscope image, and a signal transmitting unit of the relevant separation detecting and transmitting function, and thus has a function serving as one example of the in vivo imaging device. The monitor device 12 or the receiving device 13 receives the wireless signal of the separation detection result from the inserting unit 5 having such separation detecting and transmitting function.

In the first embodiment of the present invention, the image (endoscope image) captured by the endoscope or the image (capsule image) captured by the intra-body indwelling capsule is displayed on the display device, where the capsule image is displayed on the display device when the intra-body indwelling capsule is arranged at the distal end of the inserting unit of the endoscope, and the display image of the display device is switched from the capsule image to the endoscope image when the separation of the intra-body indwelling capsule from the inserting unit is detected, as described above. Therefore, an intra-subject indwelling system which has the function serving as the imaging and displaying system of switching between the captured capsule image and the endoscope image and displaying the same on the display device, and furthermore, continuously displays on the display device a series of images of the inside of the subject from when the inserting unit of the endoscope arranged with the intra-body indwelling capsule at the distal end is inserted into the subject until the intra-body indwelling capsule is placed at the desired site of the subject, easily introduces the intra-body indwelling capsule at the desired site in the subject, and places the same is realized.

In continuation to the series of images of the inside of the relevant subject, the take-out path in the subject until the inserting unit of after the intra-body indwelling capsule is separated is taken out from the subject is continuously displayed on the display device, and thus the inserting unit can be easily taken out from the subject.

Furthermore, since the detection unit for detecting the separation of the intra-body indwelling capsule from the inserting unit of the endoscope, and a wireless transmitting unit for transmitting the wireless signal containing the separation detection result are incorporated in the indwelling unit of the intra-body indwelling capsule, a multi-purpose capsule endoscope can be used as a capsule main body to be attached to the indwelling unit, whereby the time and effort necessary for realizing the intra-body indwelling capsule are reduced.

According to the present invention, the endoscope image captured by the endoscope and the capsule image captured by the intra-body indwelling capsule are switched and displayed on the display device of the endoscope system for observing (examining) the inside of the subject by inserting the inserting unit of the endoscope into the subject. Therefore, doctors, nurses, etc. are able to insert the inserting unit arranged with the intra-body indwelling capsule at the distal end to the desired site inside the subject while visually checking the display image of the display device, and place the relevant intra-body indwelling capsule at the desired site in the subject, similar to the method of working the usual endoscope examination. Furthermore, after placing the intra-body indwelling capsule at the desired site in the subject, doctors, nurses, etc. are able to take out the inserting unit from the subject while visually checking the display image of the display device, similar to the method of working the usual endoscope examination.

Second Embodiment

A second embodiment of the present invention will now be described. The separation detecting function of detecting the separation of the intra-body indwelling capsule 2 from the inserting unit 5 and the wireless transmitting function of transmitting the wireless signal containing the separation detection result of the intra-body indwelling capsule 2 have been incorporated in the indwelling unit 4 in the first embodiment, but the relevant separation detecting function and the wireless transmitting function are incorporated in the capsule main body of the intra-body indwelling capsule in the second embodiment.

Figure 11:
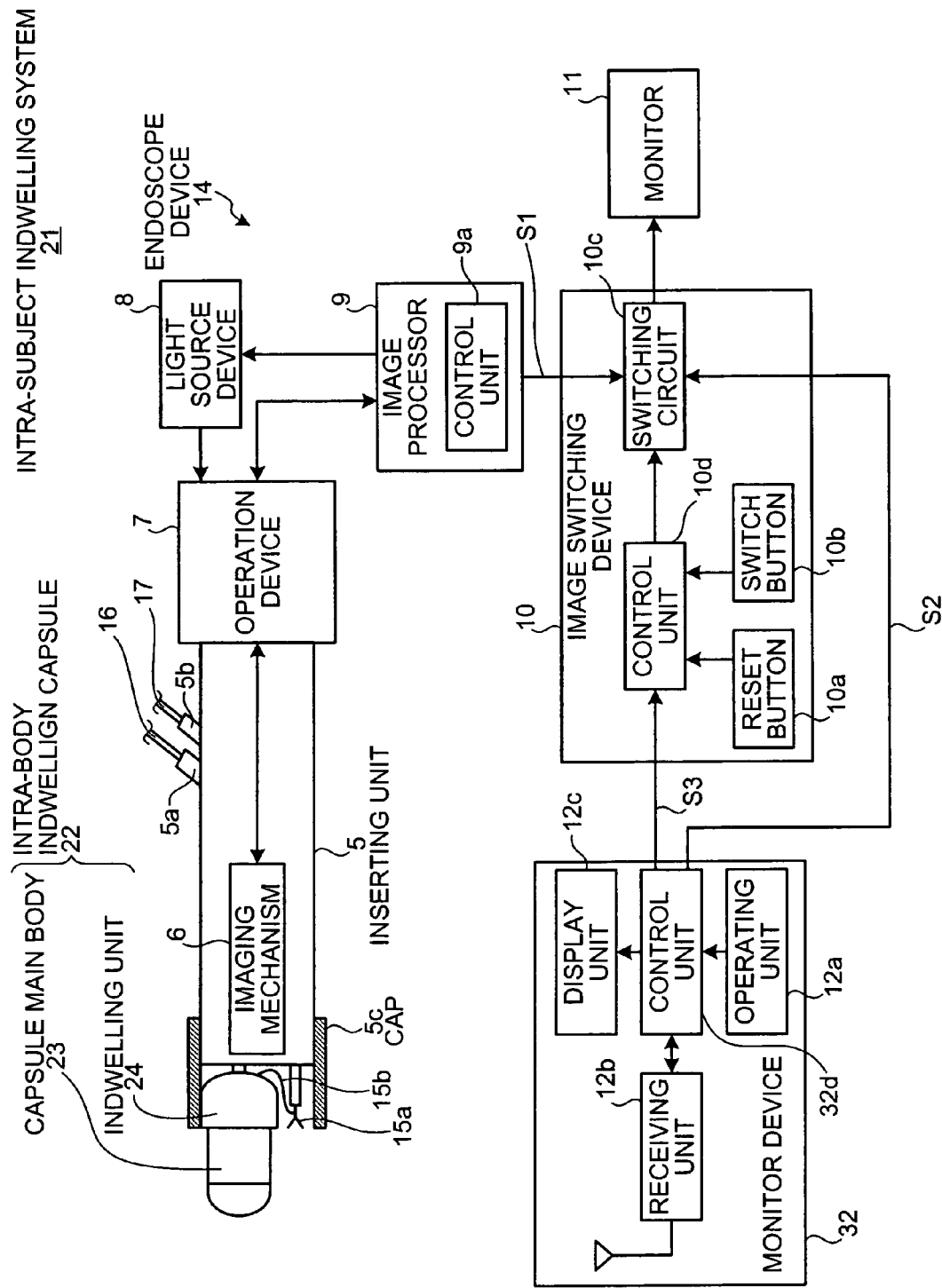
FIG. 11 is a block diagram illustrating in a frame format one configuration example of an intra-subject indwelling system, which is a second embodiment of the present invention.

FIG. 11 is a block diagram illustrating in a frame format one configuration example of an intra-subject indwelling system, which is the second embodiment of the present invention. As shown in FIG. 11, the intra-subject indwelling system 21 includes an intra-body indwelling capsule 22 in place of the intra-body indwelling capsule 2 of the intra-subject indwelling system 1 of the above described first embodiment, and includes a monitor device 32 in place of the monitor device 12. Furthermore, the receiving device 13 of the intra-subject indwelling system 1 of the first embodiment is not arranged in the intra-subject indwelling system 21, and the monitor device 32 transmits the separation detection signal S3 to the image switching device 10. Other configurations are the same as the first embodiment, and the same reference characters are denoted for the same components.

The intra-body indwelling capsule 22 is realized by attaching the indwelling unit 24 to the capsule main body 23. The capsule main body 23 has the function similar to the capsule main body 3 in the first embodiment described above, and further has a detecting function for detecting that the intra-body indwelling capsule 22 is separated from the inserting unit 5 or that the retention state is released, and the wireless transmitting function of transmitting the wireless signal containing the separation detection result notifying that the intra-body indwelling capsule 22 has separated to the outside of the subject. On the other hand, the indwelling unit 24 includes the clip 15a and the string member 15b, for example, as a device for placing the intra-body indwelling capsule 22 at the desired site in the subject. The details of the relevant capsule main body 23 and the indwelling unit 24 will be hereinafter described.

The monitor device 32 functions as one example of the in vitro device, and has a function similar to the monitor device 12 of the first embodiment described above, and further has a function of receiving the separation detection result from the capsule main body 23 via a predetermined electric wave and outputting the received separation detection result to the control unit 10d of the image switching device 10 as the separation detection signal S3. Specifically, the monitor device 32 includes a control unit 32d in place of the control unit 12d of the monitor device 12 of the first embodiment described above. The receiving unit 12b of the relevant monitor device 32 receives the wireless signal containing the image signal of the capsule image or the separation detection result via the predetermined electric wave transmitted and received with the capsule main body 23. The receiving unit 12b performs a predetermined demodulation process and the like on the wireless signal received from the capsule main body 23, and restores the image signal of the capsule image or the separation detection result based on the wireless signal. In this case, the receiving unit 12b transmits the image signal of the capsule image or the separation detection result to the control unit 32d.

The control unit 32d distinguishes the image signal of the capsule image and the signal corresponding to the separation detection result, and outputs the capsule image signal S2 corresponding to the capsule image and the separation detection signal S3 corresponding to the separation detection result, respectively, to the image switching device 10. Specifically, when receiving the image signal of the capsule image from the receiving unit 12b, the control unit 32d generates the capsule image based on the image signal, and performs the control on the monitor device 12 to display the capsule image, similar to the display unit 12c described above. Furthermore, the control unit 32d transmits the capsule image signal S2 corresponding to the capsule image to the switching circuit 10c of the image switching device 10. When receiving the separation detection result from the receiving unit 12b, the control unit 32d transmits the separation detection result to the control unit 10d of the image switching device 10 as the separation detection signal S3.

The display device for switching between the endoscope image and the capsule image and displaying the same is realized by combining the monitor device 32, the monitor 11, and the image switching device 10. Such display device functions to display the capsule image when the retaining member 16 is retaining the intra-body indwelling capsule 22 at the distal end of the inserting unit 5 (retention state), and switches from the capsule image to the endoscope image and displays the same when receiving the separation detection result notifying that the retention state is released or is separated from the distal end of the inserting unit 5.

Figure 12:
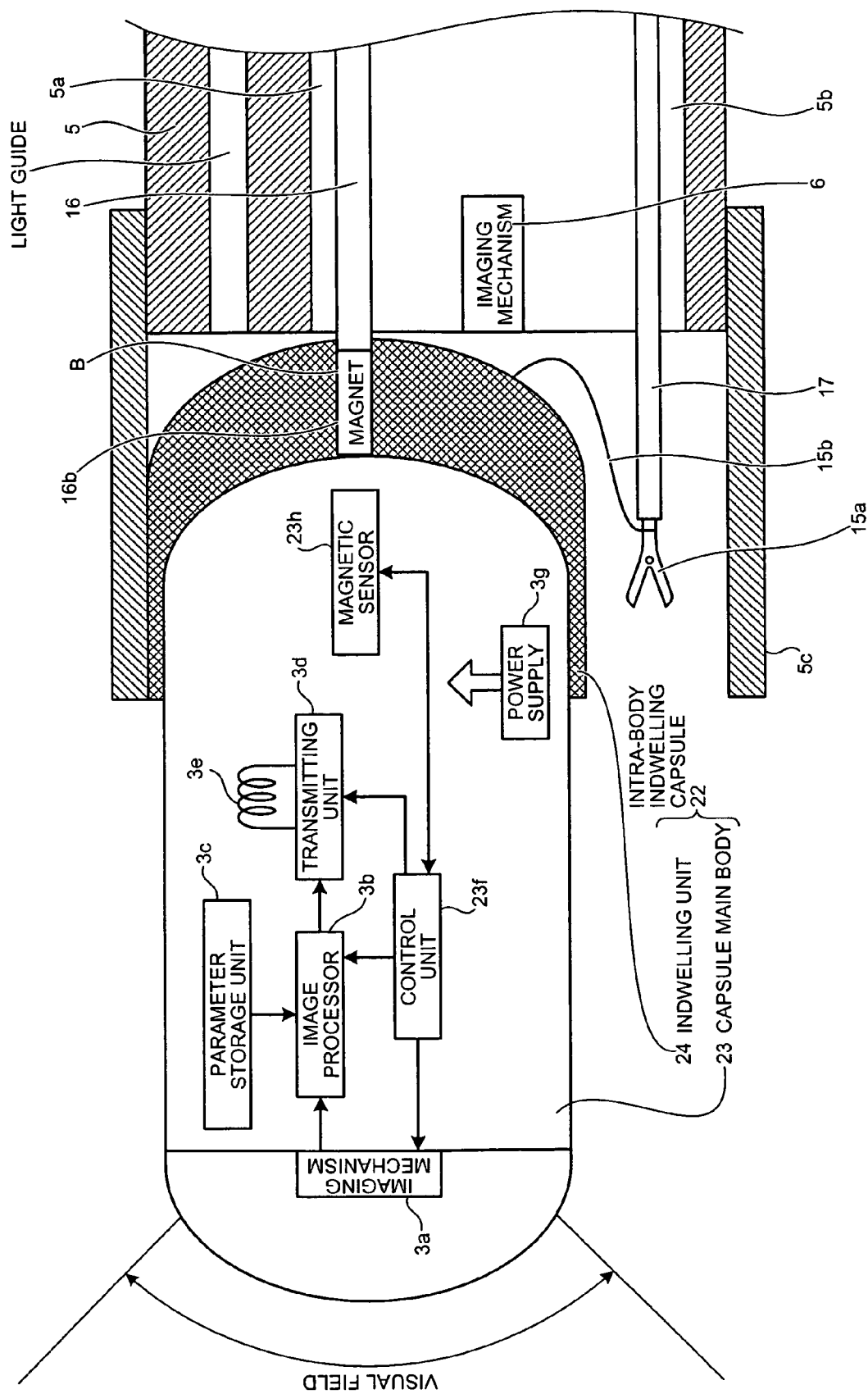
FIG. 12 is a block diagram showing in a frame format one configuration example of the intra-body indwelling capsule of the second embodiment.

The configuration of the intra-body indwelling capsule 22 will now be described in detail. FIG. 12 is a block diagram showing in a frame format one configuration example of the intra-body indwelling capsule 22. In FIG. 12, the intra-body indwelling capsule 22 in a state detachably arranged at the distal end of the inserting unit 5 is illustrated. As shown in FIG. 12, the intra-body indwelling capsule 22 is realized by attaching the indwelling unit 24 to the back end of the capsule main body 23.

The indwelling unit 24 is formed with a concave part that engages the back end of the housing the capsule main body 23 and is attached to the back end of the capsule main body 23, similar to the indwelling unit 4 of the first embodiment described above. An opening B to be detachably fitted with the retaining member 16 is formed at the back end of the indwelling unit 24. The intra-body indwelling capsule 22 is retained by the retaining member 16 fitted to the opening B, and is detachably arranged at the distal end of the inserting unit 5.

The capsule main body 23 includes a control unit 23f in place of the control unit 3f of the capsule main body 3 of the first embodiment described above, and further includes a magnetic sensor 23h. Other configurations are the same as the capsule main body 3 of the first embodiment, and thus same reference characters denote the same components. The magnetic sensor 23h detects the separation of the intra-body indwelling capsule 22 from the inserting unit 5 or the retention state release. Specifically, the magnetic sensor 23h detects the magnetic strength by the magnet 16b arranged at the distal end of the retaining member 16, and detects the take-out of the retaining member 16 based on the decreasing change in the magnetic strength that occurs when the retaining member 16 is taken out from the opening B. The intra-body indwelling capsule 22 is released from the retention state by the retaining member 16, and separated from the inserting part 5 when the retaining member 16 is taken out from the opening B of the indwelling unit 24. Therefore, the magnetic sensor 23h detects the separation of the intra-body indwelling capsule 22 from the endoscope 5 or the retention state release by detecting the take-out of the retaining member 16 based on the decreasing change in the magnetic strength by the relevant magnet 16b. The magnetic sensor 23h transmits the separation detection result of the intra-body indwelling capsule 22 to the control unit 23f.

The control unit 23f controls the drive of the imaging mechanism 3a, the image processing section 3b, and the transmitting unit 3d, similar to the control unit 3f of the capsule main body 3 of the first embodiment described above, and further controls the drive of the magnetic sensor 23h. When receiving the separation detection result of the intra-body indwelling capsule 22 from the magnetic sensor 23, the control unit 23f transmits the received separation detection result to the transmitting unit 3d, and performs the control on the transmitting unit 3d to transmit the wireless signal corresponding to the separation detection result to the outside. The transmitting unit 3d generates the wireless signal containing the separation detection result and outputs the generated wireless signal to the transmitting antenna 3e based on the control of the relevant control unit 23f. In this case, the transmitting antenna 3e outputs the wireless signal input by the transmitting unit 3d to the outside. The wireless signal output in this manner is received at the receiving unit 12b of the monitor device 32, as described above. In other words, the transmitting unit 3d and the transmitting antenna 3e function as the wireless transmitting unit for transmitting the wireless signal containing the image signal of the capsule image, and also function as the wireless transmitting unit for transmitting the wireless signal containing the separation detection result.

Figure 13:
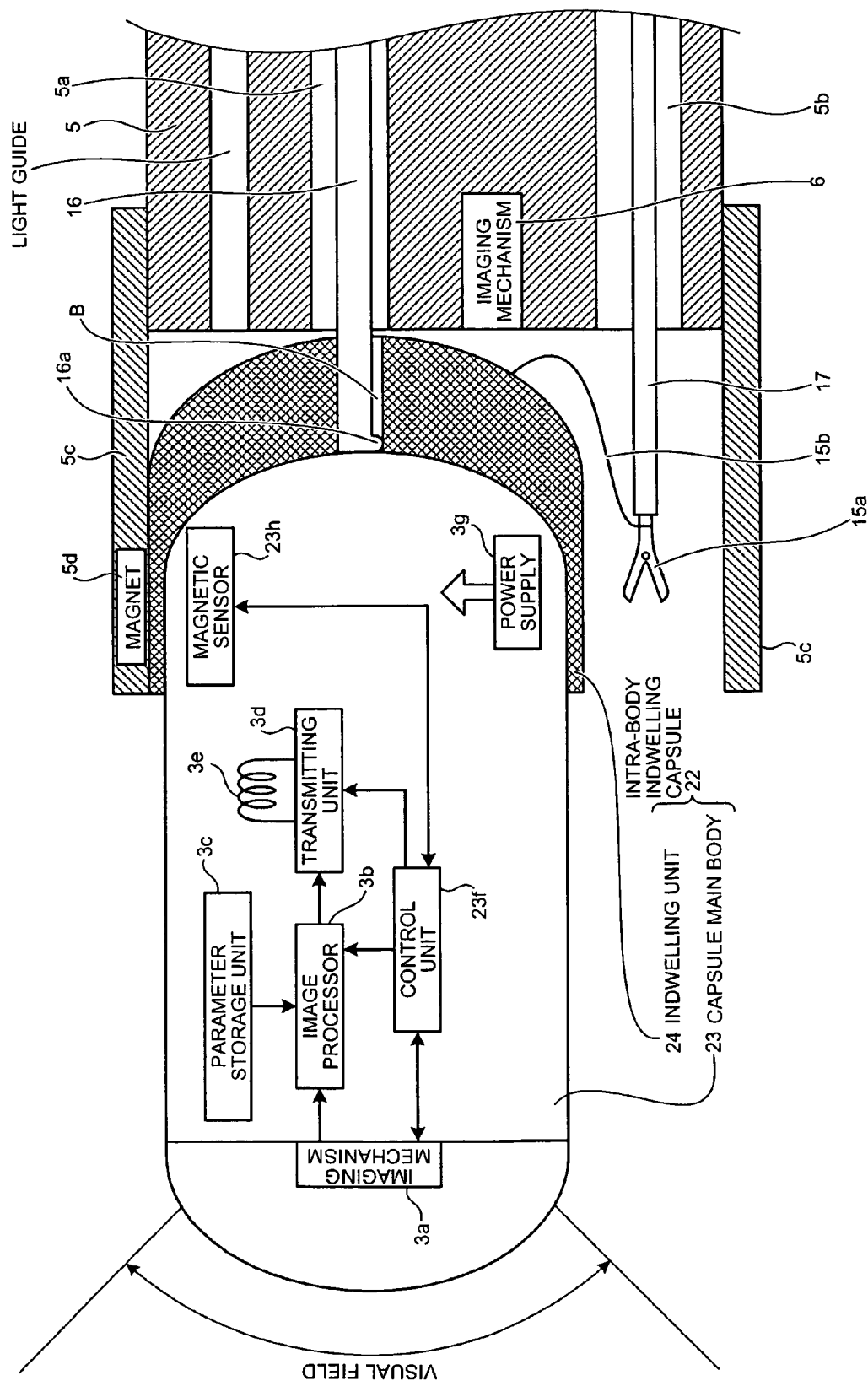
FIG. 13 is a block diagram showing in a frame format a variant of the intra-body indwelling capsule of the second embodiment.

The separation of the intra-body indwelling capsule 22 is detected by detecting the take-out of the retaining member 16 from the indwelling unit 24 in the second embodiment of the present embodiment, but the present invention is not limited thereto, and the separation of the intra-body indwelling capsule 22 may be detected by detecting that the capsule main body 23 has separated from the distal end of the inserting unit 5 by greater than or equal to a predetermined distance. Specifically, as shown in FIG. 13, a magnet 5d is arranged at the cap 5c of the distal end of the inserting unit 5, and the magnetic sensor 23h of the capsule main body 23 is incorporated on the side contacting the cap 5c, that is, in the vicinity of the magnet 5d. In this case, the magnetic sensor 23h detects the change in strength of magnetism by the magnet 5d and detects that the capsule main body 23 has separated from the inserting unit 5 by greater than or equal to a predetermined distance based on the decreasing change in the magnetic strength that occurs when the distance between the capsule main body 23 and the distal end (specifically, magnet 5d) of the inserting unit 5 is separated by greater than or equal to a predetermined value. The magnetic sensor 23h detects the separation of the intra-body indwelling capsule 22 by detecting the spacing apart of the capsule main body 23 and the inserting unit 5. In this case, the control unit 23f receives the separation detection result of the intra-body indwelling capsule 22 from the magnetic sensor 23h.

The take-out of the retaining member 16 is detected based on the decreasing change in the magnetic field strength that occurs when the retaining member 16 is taken out from the opening B of the indwelling unit 24 in the second embodiment of the present embodiment, but the present invention is not limited thereto, and the take-out of the retaining member 16 may be detected based on the change in pressure that occurs when taking out the retaining member 16 from the indwelling unit 24. In this case, the opening B of the indwelling unit 24 is made into a pass through hole, and the retaining member 16 is pushed into the pass through hole so that the distal end of the retaining member 16 is pressed against the back end of the capsule main body 23 engaged to the indwelling unit 24. A pressure sensor is incorporated in the capsule main body 23 in place of the magnetic sensor 23h. The pressure sensor detects the pressure applied to the back end of the capsule main body 23 when the retaining member 16 is pressed against thereto. The applied pressure decreases with the take-out of the retaining member 16, and thus the pressure sensor detects the take-out of the retaining member 16 based on the lowering change of the pressure.

The endoscope device 14 formed with two forceps channels is used in the second embodiment of the present invention, but the present invention is not limited thereto, and an endoscope formed with one or more forceps channel may be applied.

The separation detecting and transmitting function of detecting the retention state release or the separation of the intra-body indwelling capsule 22 and wirelessly transmitting the separation detection result has been arranged on the intra-body indwelling capsule 22 side (specifically, in the capsule main body 23) in the second embodiment of the present invention, but the present invention is not limited thereto, and the separation detecting and transmitting function may be incorporated on the endoscope device 14 side, that is, in the vicinity of the distal end of the inserting unit 5. In this case, the endoscope device 14 having the relevant separation detecting and transmitting function includes the imaging mechanism 6 for imaging the endoscope image and the signal transmitting unit of the separation detecting and transmitting function, and thus has a function serving as one example of the in vivo imaging device. The monitor device 32 receives the wireless signal of the separation detection result from the inserting unit 5 having the separation detecting and transmitting function.

As described above, in the second embodiment of the present invention, the endoscope image or the capsule image is displayed on the display device, where the capsule image is displayed on the display device when the intra-body indwelling capsule is arranged at the distal end of the inserting unit of the endoscope, and the display image of the display device is switched from the capsule image to the endoscope image when the separation of the intra-body indwelling capsule from the inserting unit is detected, similar to the first embodiment described above. The separation detecting function of the intra-body indwelling capsule is incorporated in the capsule main body, and the capsule image or the separation detection result is wirelessly transmitted using the wireless transmitting function of the capsule main body. Therefore, the separation detection result is received by the image receiving device (e.g., monitor device 32) for receiving the capsule image from the capsule main body without arranging a dedicated receiving device for receiving the wireless signal containing the separation detection result, thereby benefiting the effect of the first embodiment described above, and realizing the intra-subject indwelling system that promotes miniaturization of the system scale.

INDUSTRIAL APPLICABILITY

The in vivo imaging device, the display device, the imaging and displaying system using the same, and the intra-subject indwelling system are effective in imaging and observing a desired site (e.g., affected area, operative scar etc.) inside the subject such as a patient, and in particular, is suited for a, medical system for introducing and placing the intra-body indwelling capsule at the desired site of the subject.

The invention claimed is:

1. An intra-subject indwelling system comprising:
    an endoscope device that includes an inserting unit to be inserted into a subject, captures a first image of an inside of the subject from a distal end of the inserting unit, and outputs the captured first image;
    an intra-body indwelling capsule endoscope that is detachably arranged at the distal end of the inserting unit, the intra-body indwelling capsule endoscope comprising:
    a separation detector configured to detect a separation of the intra-body indwelling capsule endoscope, in the subject, from the inserting unit,
    a transmitter configured to transmit a separation detection result generated by the separation detector, the separation detection result being transmitted to an outside of the subject, and
    a image capturing device configured to capture a second image of the inside of the subject, for transmission to the outside of the subject;
    an in vitro receiving device that receives one of the separation detection result and the second image transmitted to the outside of the subject;

a monitor that displays one of the first image and the second image; and an image switching device that receives the first image and the second image, and switches an image to be displayed on the monitor from the second image to the first image when receiving the separation detection result.

2. The intra-subject indwelling system according to claim 1, wherein the image switching device makes the second image an image to be displayed on the monitor for an initial state of the case where the intra-body indwelling capsule endoscope is arranged at the distal end of the inserting unit.

3. A method comprising:

capturing a first image of an inside of a subject to output the captured first image from the endoscope device by an endoscope device, the endoscope device including an inserting unit to be inserted into the subject, the first image being captured from a distal end of the inserting unit;

detecting a separation of an intra-body indwelling capsule endoscope, in the subject, from the inserting unit by a separation detector disposed in the intra-body indwelling capsule endoscope, the intra-body indwelling capsule endoscope being detachably arranged at the distal end of the inserting unit;

transmitting a separation detection result by a transmitter disposed in the intra-body indwelling capsule endoscope for notifying the separation to an outside of the subject;

capturing a second image of the inside of the subject by an image capturing device disposed in the intra-body indwelling capsule endoscope;

transmitting the captured second image to the outside of the subject by the intra-body indwelling capsule endoscope;

receiving one of the separation detection result and the second image transmitted to the outside of the subject by an in vitro receiving device;

displaying one of the first image and the second image on a monitor;

receiving the first image and the second image by an image switching device; and switching an image to be displayed on the monitor from the second image to the first image when receiving the separation detection result, by the image switching device.

4. The method according to claim 1, where an initial image displayed on the monitor in a state where the intra-body indwelling capsule endoscope is arranged at the distal end of the inserting unit is the second image.

\* \* \* \* \*